United States Patent
Zelinsky

(10) Patent No.: US 7,607,777 B2
(45) Date of Patent: Oct. 27, 2009

(54) METHOD FOR DIAGNOSIS AND TREATMENT OF PROCESSING DIFFICULTIES, INTEGRATION PROBLEMS, IMBALANCES AND ABNORMAL POSTURES

(75) Inventor: Deborah Zelinsky, 244 Lagoon Dr., Northfield, IL (US) 60093

(73) Assignee: Deborah Zelinsky, Northfield, IL (US)

( * ) Notice: Subject to any disclaimer, the term of this patent is extended or adjusted under 35 U.S.C. 154(b) by 0 days.

(21) Appl. No.: 12/191,508

(22) Filed: Aug. 14, 2008

(65) Prior Publication Data

US 2009/0005702 A1  Jan. 1, 2009

Related U.S. Application Data

(62) Division of application No. 11/384,912, filed on Mar. 20, 2006, now Pat. No. 7,427,136.

(60) Provisional application No. 60/663,131, filed on Mar. 18, 2005.

(51) Int. Cl.
*A61B 3/00* (2006.01)
*A61B 5/05* (2006.01)
(52) U.S. Cl. ................... 351/219; 600/356
(58) Field of Classification Search ............ 351/200, 351/219, 246–247; 600/356
See application file for complete search history.

(56) References Cited

U.S. PATENT DOCUMENTS

2002/0198453 A1  12/2002  Herrick, II

2004/0141151 A1*  7/2004  Gillespie .................. 351/200
2005/0240147 A1  10/2005  Makower et al.

OTHER PUBLICATIONS

Odyssey Medical, Inc., "Do You Suffer From Dry Eye Syndrome?" 2002.
Zelinsky O.D., Debroah, "The Mind-Eye Connection—An Insight To Vision: A Guide to Understanding Neuro-Optometry's Pivotal Role in Patient Rehabilitation", (2004).
Odyssey Medical, Inc., "Parasol Punctal Occluder system—Physician Instructions" (Jun. 2004).
Detroit Free Press, "This Optometrist Gets Eyes in Line" (Aug. 2005).
Deirne, Michael, "New Options in Punctal Occlusion", undated.
Appelbaum, Stanley A. OD, FCOVD, "Head Injury and Stroke Vision Rehabilitation", undated.
Aging Eye Times Information Sheet, undated.

* cited by examiner

*Primary Examiner*—Scott J Sugarman
*Assistant Examiner*—Dawayne A Pinkney
(74) *Attorney, Agent, or Firm*—K&L Gates LLP

(57) ABSTRACT

Methods for diagnosis and treatment are provided for a patient having processing difficulties, integration problems, imbalances or abnormal postures. In one embodiment, a patient is identified having retinal signal problems creating at least one negative medical condition. Then, at least a portion of the patient's lacrimal drainage system is blocked or altered. Further, as a result of the diagnosis and treatment, the patient achieves improved retinal signal processing and at least one of the patient's negative medical conditions is improved. Other embodiments include using in combination the Z-Bell Test and/or light blocking or altering devices for diagnosis and treatment.

27 Claims, 26 Drawing Sheets

RETINAL PROCESSING PATHWAYS

FIG. 7B

| Name: | Diagnosis: | File: |
|---|---|---|
| ID: | Operator: | Date: 1/27/2006 |
| Date of Birth: | Referral Source: | Time: 12:34:34 |
| Height: | Comments: | |

Sensory Organization Test COG Trace

|  | Trial 1 | Trial 2 | Trial 3 |
|---|---|---|---|
| Normal Vision Fixed Surface | + | + | + |
| Absent Vision Fixed Surface | + | + | + |
| SwayRef Vision Fixed Surface | + | + | + |
| Normal Vision SwayRef Surface | + | ⊣ | ⊦ |
| Absent Vision SwayRef Surface | ⟆ | ⟆ | ⟆ |
| SwayRef Vision SwayRef Surface | ⟆ | ⟆ | ⟆ |

⊥ 10 degrees

FIG. 7C

Name:              Diagnosis:              File:
ID:                      Operator:
Date of Birth:        Referral Source:
Height:      Comments:

Sensory Organization Test

Test Date: 1/27/2006
Test Time: 12:34:34

| Conditions | EQUILIBRIUM | | | STRATEGY | | | COG Alignment | | |
|---|---|---|---|---|---|---|---|---|---|
| | Trial 1 | Trial 2 | Trial 3 | Trial 1 | Trial 2 | Trial 3 | Trial 1 | Trial 2 | Trial 3 |
| 1 | 87 | 87 | 88 | 96 | 97 | 98 | -0.1 0.1 | -0.2 1.0 | -0.1 0.7 |
| 2 | 87 | 86 | 83 | 96 | 96 | 95 | 0.1 0.8 | 0.1 0.1 | 0.0 -0.1 |
| 3 | 88 | 90 | 92 | 97 | 98 | 98 | 0.2 0.2 | 0.2 0.7 | 0.2 0.3 |
| 4 | 77 | 51 | 51 | 83 | 76 | 77 | 0.3 -0.3 | -0.1 -0.1 | -0.1 -0.6 |
| 5 | 59 | 38 | 37 | 73 | 66 | 70 | -0.1 0.1 | 0.2 1.0 | 0.0 0.6 |
| 6 | 12 | 26 | 32 | 34 | 66 | 66 | 0.0 0.4 | 0.5 0.7 | 0.0 0.1 |

Composite = 59

FIG. 7D
Name:      Diagnosis:      File:
ID:      Operator:      Date: 12/6/2005
Date of Birth:      Referral Source:      Time: 10:11:14
Height:      Comments:
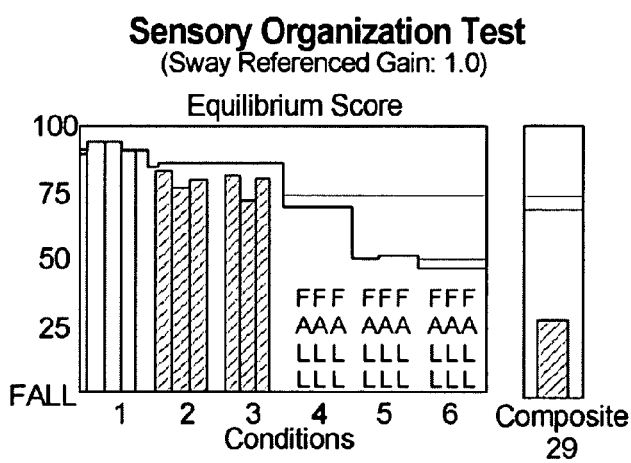
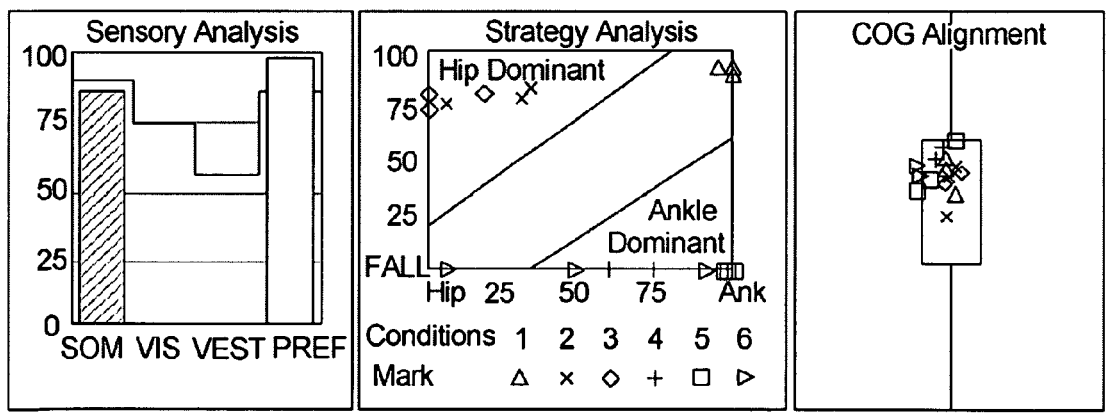
Data Range Note: User Data Range: 20-59
Post Test Comment:

FIG. 7E

| Name: | Diagnosis: | File: |
| --- | --- | --- |
| ID: | Operator: | Date: 12/6/2005 |
| Date of Birth: | Referral Source: | Time: 10:11:14 |
| Height: | Comments: | |

Sensory Organization Test COG Trace

|  | Trial 1 | Trial 2 | Trial 3 |
| --- | --- | --- | --- |
| Normal Vision Fixed Surface | ✦ | ✦ | ✦ |
| Absent Vision Fixed Surface | ✦ | ✵ | ✵ |
| SwayRef Vision Fixed Surface | ✦ | ✵ | ✵ |
| Normal Vision SwayRef Surface | ～ FALL | ⋏ FALL | ⋏ FALL |
| Absent Vision SwayRef Surface | ∫ FALL | ⋏ FALL | ⋏ FALL |
| SwayRef Vision SwayRef Surface | ⋎ FALL | ⋏ FALL | ⋏ FALL |

10 degrees

FIG. 7G

Name:           Diagnosis:           File:
ID:           Operator:
Date of Birth:           Referral Source:
Height:     Comments:

Sensory Organization Test

Test Date: 12/6/2005
Test Time: 10:11:14

| Conditions | EQUILIBRIUM Trial 1 | Trial 2 | Trial 3 | STRATEGY Trial 1 | Trial 2 | Trial 3 | COG Alignment Trial 1 | | Trial 2 | | Trial 3 | |
|---|---|---|---|---|---|---|---|---|---|---|---|---|
| 1 | 93 | 93 | 90 | 100 | 95 | 100 | 0.0 | 1.2 | 0.0 | 1.5 | 0.3 | 0.5 |
| 2 | 83 | 76 | 79 | 34 | 7 | 31 | 0.0 | -0.1 | 0.3 | 1.3 | 0.0 | 0.9 |
| 3 | 81 | 72 | 80 | 19 | 0 | 0 | 0.5 | 1.1 | 0.1 | 1.2 | 0.0 | 0.8 |
| 4 | FALL | FALL | FALL | 0 | 74 | 59 | -0.3 | 1.5 | -0.1 | 1.5 | -0.1 | 1.8 |
| 5 | FALL | FALL | FALL | 97 | 100 | 98 | 0.3 | 2.0 | -0.5 | 0.9 | -0.9 | 0.6 |
| 6 | FALL | FALL | FALL | 91 | 8 | 49 | -0.9 | 1.3 | -0.9 | 1.3 | -0.8 | 1.0 |

Composite = 29

FIG. 7I

| Name: | Diagnosis: | | File: |
|---|---|---|---|
| ID: | Operator: | | |
| Date of Birth: | Referral Source: | | |
| Height: | Comments: | | |

Adaptation Test

Test Date: 12/6/2005
Test Time: 10:26:38

| Conditions | Trial 1 | Trial 2 | Trial 3 | Trial 4 | Trial 5 |
|---|---|---|---|---|---|
| TOES UP | 82 | 90 | 77 | 58 | 45 |
| TOES DOWN | FALL | FALL | FALL | 149 | 76 |

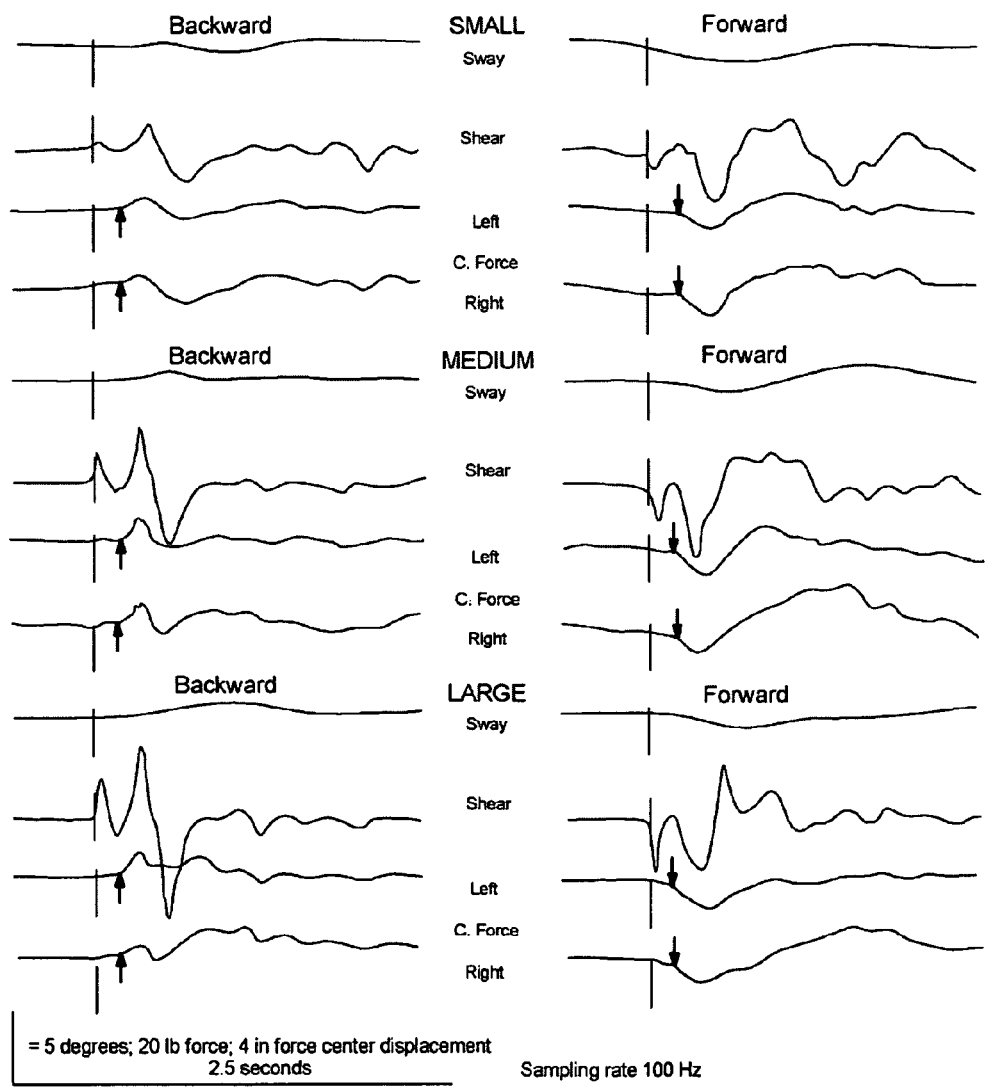

FIG. 7M

Name:  Diagnosis:  File:
ID:  Operator:
Date of Birth: 5/14/1948  Referral Source:
Height:  Comments:

Motor Control Test

Test Date: 12/6/2005
Test Time: 10:22:54

| Translation | WEIGHT SYMMETRY | Latency (msec) Left | Right | AMPLITUDE SCALING Left | Right | STRENGTH SYMMETRY |
|---|---|---|---|---|---|---|
| Small B | 98 | 150 4 | 160 4 | 2 | 2 | 100 |
| Medium B | 98 | 160 4 | 140 4 | 4 | 4 | 100 |
| Large B | 101 | 150 4 | 150 4 | 5 | 6 | 109 |
| Small F | 95 | 170 3 | 180 2 | 2 | 3 | 120 |
| Medium F | 109 | 150 4 | 170 4 | 4 | 5 | 111 |
| Large F | 109 | 140 2 | 140 4 | 4 | 4 | 100 |

Composite = 150

FIG. 7N
Name:    Diagnosis:    File:
ID:    Operator:    Date: 1/27/2006
Date of Birth:    Referral Source:    Time: 12:12:26
Height:    Comments:
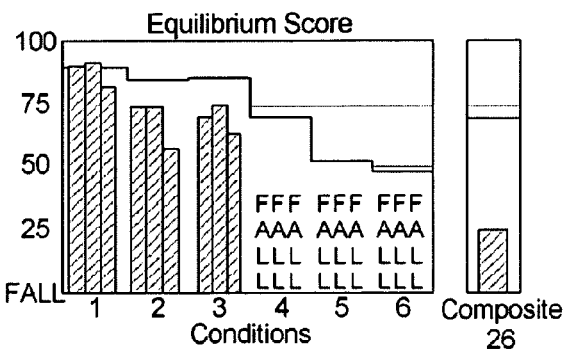
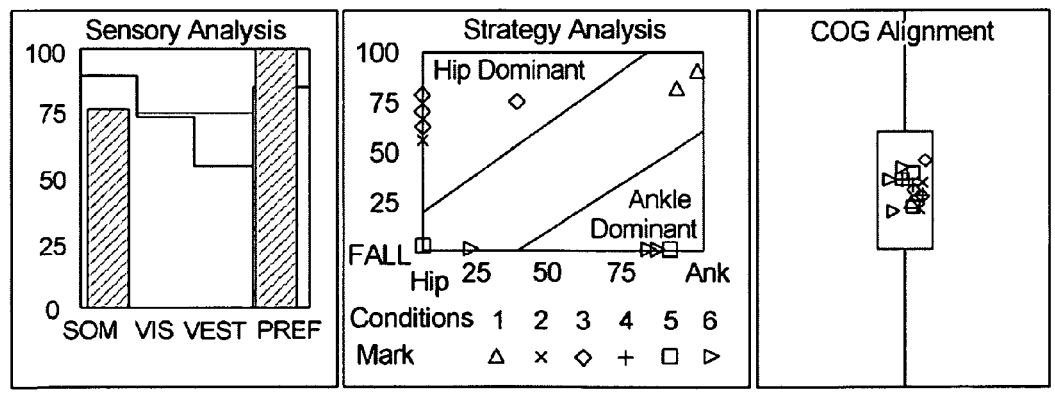
Data Range Note: User Data Range: 20--59
Post Test Comment:

FIG. 7O

Name:           Diagnosis:           File:
ID:           Operator:
Date of Birth:           Referral Source:
Height:       Comments:

Pre drops

Sensory Organization Test

Test Date: 1/27/2006
Test Time: 12:12:26

|  | EQUILIBRIUM | | | STRATEGY | | | COG Alignment | | |
| --- | --- | --- | --- | --- | --- | --- | --- | --- | --- |
| Conditions | Trial 1 | Trial 2 | Trial 3 | Trial 1 | Trial 2 | Trial 3 | Trial 1 | Trial 2 | Trial 3 |
| 1 | 90 | 91 | 82 | 98 | 98 | 91 | 0.4 -0.1 | 0.8 0.3 | 0.8 0.1 |
| 2 | 73 | 73 | 56 | 0 | 0 | 0 | 0.7 -0.3 | 0.8 0.5 | 0.8 0.5 |
| 3 | 69 | 74 | 62 | 0 | 34 | 0 | 0.5 0.3 | 0.9 1.2 | 0.8 0.1 |
| 4 | FALL | FALL | FALL | 64 | 69 | 91 | 0.1 0.6 | 0.7 -0.2 | 0.5 0.4 |
| 5 | FALL | FALL | FALL | 89 | 0 | 0 | 0.1 0.6 | 0.5 0.8 | 0.5 -0.2 |
| 6 | FALL | FALL | FALL | 82 | 85 | 18 | -0.3 0.6 | 0.1 1.0 | -0.2 -0.4 |

Composite = 26

FIG. 7P

Name:          Diagnosis:          File:
ID:             Operator:          Date: 1/27/2006
Date of Birth:    Referral Source:    Time: 12:12:26
Height:       Comments:

Sensory Organization Test COG Trace     pre drops

|  | Trial 1 | Trial 2 | Trial 3 |
|---|---|---|---|
| Normal Vision Fixed Surface |  |  |  |
| Absent Vision Fixed Surface |  |  |  |
| SwayRef Vision Fixed Surface |  |  |  |
| Normal Vision SwayRef Surface | FALL | FALL | FALL |
| Absent Vision SwayRef Surface | FALL | FALL | FALL |
| SwayRef Vision SwayRef Surface | FALL | FALL | FALL |

⊥ 10 degrees

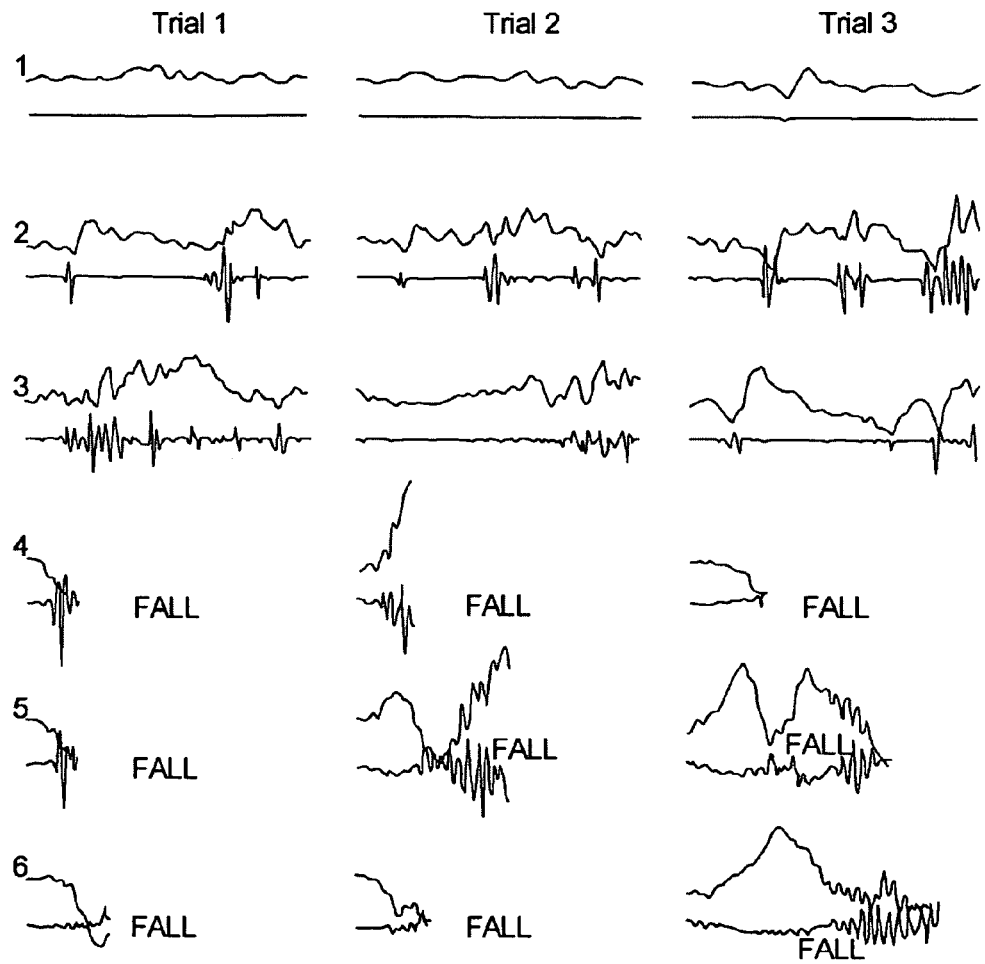

FIG. 7R
Name:  Diagnosis:  File:
ID:  Operator:  Date: 1/27/2006
Date of Birth:  Referral Source:  Time: 12:34:34
Height:  Comments:
Sensory Organization Test
(Sway Referenced Gain: 1.0)
post plugs
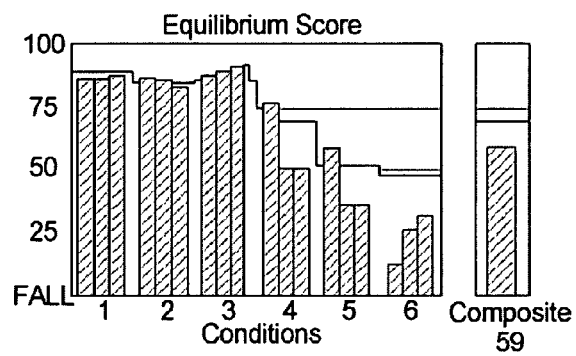
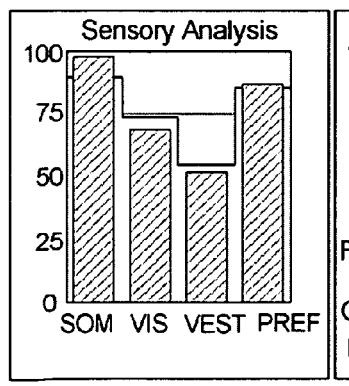 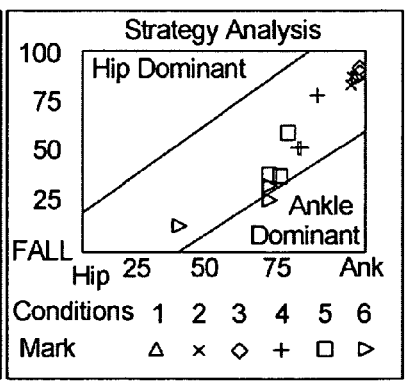 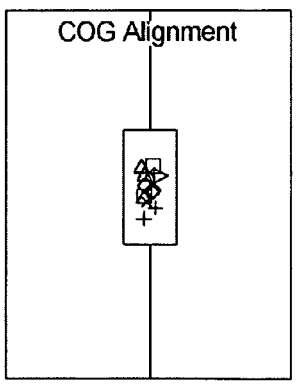
Data Range Note: User Data Range: 20–59
Post Test Comment:

FIG. 8

| | | Optometric Intervention | | Expected Responses and Perceptions | | Skills Affected |
|---|---|---|---|---|---|---|
| Balance (Where am I?) | BODY Brainstem Cerebellum and Limbic System | Yoked prism (phoria measurements) | BD | Eyes up and outward | Leans on heels | Motor skills |
| | | | BU | Eyes down and inward | Leans on toes | |
| | | | BR | Eyes left | Rotates body left | |
| | | | BL | Eyes right | Rotates body right | |
| Peripheral (Where is it?) ↕ Perception ↕ Central (What is it?) | ENVIRONMENT Occipital Temporal and Parietal Lobes and Limbic System (Sensory integration) | Yoked prisms also modify environmental awareness | BD | Uphill, farther and bigger (Perceptions) | | Organization skills |
| | | | BU | Downhill, closer and smaller | | |
| | | | BR | Expands space right and contracts left | | |
| | | | BL | Expands space left and contracts right | | |
| | | Non-yoked prism (vergence ranges) | BI | Objects appear farther and bigger | Shoulders back | |
| | | | BO | Objects appear closer and smaller | Shoulders forward | |
| | | Lenses (accommodative ranges) | + | Panoramic view emphasizes background | Neck muscles loosen | |
| | | | − | Tunnel vision emphasizes figure | Neck muscles tighten | |
| | | | Occlusion | Alters retinal fiber input | Alters parietal or temporal lobe input | |
| | | Filters | Tints | Shorter wave lengths | Calming (↑ parasympathetic) ↑ accommodation | |
| | | | | Longer wave lengths | Stimulating (↑ sympathetic) ↓ accommodation | |
| | | Punctal Plugs | | Effects of tear layer changes on peripheral retina being researched | | |
| Emotions (What do I Feel?) ↕ Cognition (What Will I Do About it?) | MIND Limbic System Frontal Lobe | Visual thinking games | | Differentiation of "big picture" versus details | | Visualization skills |
| | | | | Enhanced control over actions | | |
| | | | | Improved range of flexibility | | |
| | | | | Altering self-image | | |

FIG. 10

Z-BELL TEST SCORING (AUDITORY AND VISUAL)

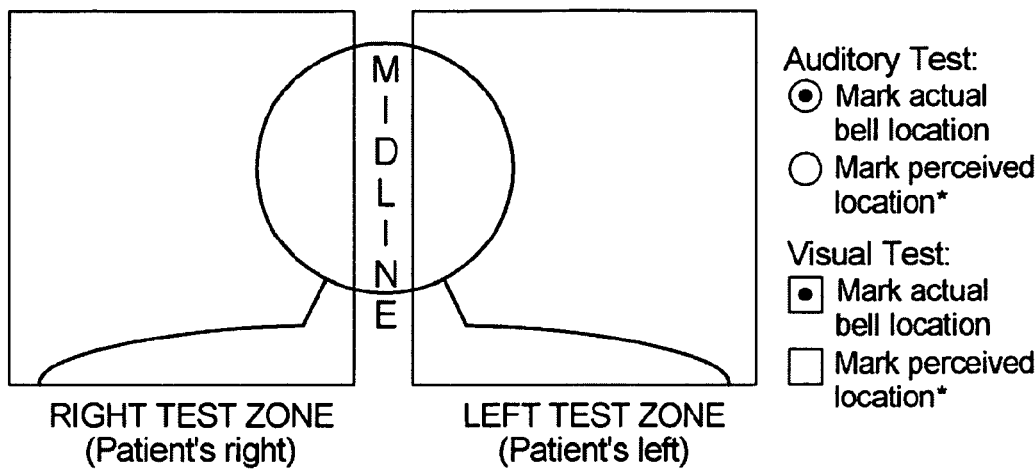

RIGHT TEST ZONE (Patient's right)  LEFT TEST ZONE (Patient's left)

Auditory Test:
● Mark actual bell location
○ Mark perceived location*

Visual Test:
[■] Mark actual bell location
[ ] Mark perceived location*

Z-Bell Auditory Test Score

Accuracy: _____

Supplemental: _____

_____

_____

Z-Bell Visual Test Score

Accuracy: _____

Supplemental: _____

_____

_____

ACCURACY SCALE
4 = accurate on first attempt
3 = accurate after readjusting once or twice
2 = accurate after 3 or more attempts
1 = tries to locate but can't
0 = No idea where located; won't attempt

* Write the accuracy score inside each circle or square that represents a perceived location.

SUPPLEMENTAL
Record any postural changes, particularly of the neck and shoulders, any unusual movements, and which hand the patient uses. Also note if a tinted lens was used, or if lenses or prisms disoriented the person's locating ability.

METHOD FOR DIAGNOSIS AND TREATMENT OF PROCESSING DIFFICULTIES, INTEGRATION PROBLEMS, IMBALANCES AND ABNORMAL POSTURES

CROSS REFERENCE TO RELATED APPLICATIONS

This application is a divisional of U.S. patent application Ser. No. 11/384,912, filed on Mar. 20, 2006, which claims the benefit of U.S. Provisional Application No. 60/663,131 filed Mar. 18, 2005.

BACKGROUND

The present invention relates to methods for diagnoses and treatments of processing difficulties, integration problems, imbalances and abnormal postures, including, but not limited to, visual and non-visual retinal signal processing problems, through Z-Bell Test diagnosis, and modification of the puncta and other parts of the lacrimal system, and/or other modifications of eye moisture and light-eye interaction using each of the following techniques and interventions or combinations of the following techniques and interventions: Z-Bell Test, partial or total blocking of the puncta or lacrimal canaliculi using punctal or lacrimal plugs, opaque or colored or non-colored contact lenses, translucent or enhancer tinted contact lenses, visible tint contact lenses, eyeglass lenses with or without tints or filters or prisms, occluders, neutral density or other types of filters, prisms, tear dye, partial or total blocking of light to the eye, i.e. visors or other types of non-lacrimal occluders, blinders, filters or other partial or total blocking or redirecting of light to the eye and/or modification of posture, head position and/or muscle tension.

Traditional methods for diagnosis and treatment of processing difficulties, integration problems, imbalances and abnormal postures of various types are known in the art and fail to address and work with the more than 160,000 peripheral retinal fibers in each eye that connect to parts of the brain and that have nothing to do with eyesight but instead are connected to the midbrain and the limbic system where all of the non-visual sensory input systems link. Also, traditional methods fail to address the linkages of all of the seven sensory systems: visual, auditory, vestibular, proprioceptive, tactile, olfactory and gustatory, and other parts of the somatosensory system, and instead focus on only the linkages of three or four systems and, even those, not in connection with the peripheral retinal fibers.

Traditional methods treat these sensory integration and processing problems internally, for example, with medications such as muscle relaxers, anti-depressants and stimulants and externally, for example, by hearing aids, standard eyeglasses, orthotics, removal of allergens, physical and sensory therapies and behavior modifications.

The standard method of optometric care is to use lenses to correct central eyesight. The traditional optometrist will prescribe the lenses that create the best central vision for a patient. If the patient still has problems then, perhaps, the optometrist will try a non-yoked prism, a tint or other occluder or, but rarely and for a different purpose, a yoked prism. This is a very limited method for diagnosis and treatment, primarily because it ignores the peripheral retina. In contrast, a feature of the method of the present invention is to not begin by treating central vision, but rather, for example, to start with a yoked prism which bends the light up or down or at an angle from the side. This triggers a reflex in the eyes pointing in the direction of the light, which in turn causes the head to follow, then the body to turn and twist to follow the light, thus shifting the center of gravity and the weight bearing posture of the patient and therefore demonstrating a reflex reaction between the retinal pathways and the body. Sometimes putting a yoked prism on a patient replaces the need for standard lenses. The yoked prism makes the patient tip his head in a different way and he can then see more clearly and more comfortably. Concomitant with this intervention, the stability of sensory integration and retinal receptor sensitivity and/or its dysfunction can be evaluated by using the Z-Bell Test, which is a diagnostic method within the present invention.

There are limitations to the standard eye evaluation because it is performed behind a phoropter where the head position is not necessarily habitual and the side vision is limited. Therefore, the peripheral retinal sensors are receiving but minimal light and are not being tested. Also, when seated in an examination chair, the patient is not required to balance against gravity or to react quickly. Virtually all testing is at a cortical level, requiring the patient to consciously answer questions.

Out of machine testing does determine the existence of peripheral vision but not its use or interaction with central eyesight. Yet, the most recent research shows that the peripheral retinal receptors are much more involved in how the central visual system is used and, therefore, the interaction of peripheral and central systems is critical to a patient's response to environmental changes.

The retina is an extension of brain tissue, converting light energy into electrical signals that are transmitted to precisely mapped sections in various regions of the brain. A significant portion of the retinal sensors transmits information to non-visual centers. There are many connections between the retina and the other senses. Light entering the eye instantly stimulates the brain at a reflexive, subcortical level and a responsive, cortical level. The subcortical pathways connecting the retina to the limbic system and the midbrain react faster than the cortical visual signals. Neither these unconscious pathways nor the interaction between sensory inputs is being evaluated during a standard visual evaluation.

Beyond the traditional methods of treatment, the state of the art includes non-traditional, marginal treatments such as the Bolles Sensory Learning Program and Stewart's Sensory-View machine, Maxsight contact lenses, and Irlen filters. While these methods do go beyond normal treatment protocols to address sensory integration problems, they also are limiting and deficient in that they fail to address linkages and therefore diagnoses and treatments affecting all seven sensory systems: visual, auditory, vestibular, proprioceptive, tactile, olfactory and gustatory, and other parts of the somatosensory system. They focus only on the linkages of, at most, three or four systems and, even those, not in connection with the peripheral retinal fibers and eye moisture. Bolles attempts to link only auditory, visual and vestibular input and Stewart measures how a patient perceives surrounding space and, therefore, orientation, but fails to address either alterations of amount and direction of entering light and alteration of eye moisture.

SUMMARY

The present inventions overcome these and other problems inherent in existing treatment and diagnosis methods. Certain methods provide, by way of example, for treatment and diagnosis through Z-Bell Test evaluations, modification of eye moisture and light-eye interaction using various treatments and interventions including, but not limited to, using punctal or lacrimal plugs, colored or tinted contact lenses, eyeglasses, prisms, tear dye, partial or total blocking of light to the eye and modification of head position, posture and muscle tension. Visors, blinders and filters can also achieve positive treatment benefits by altering the balance between magnocellular and parvocellular pathways. The methods and techniques focus on the more than 160,000 peripheral retinal fibers that connect to parts of the brain that are linked to the tectum, pretectum, midbrain and limbic system. Also, the diagnoses and treatments address the linkages of all seven sensory systems: visual, auditory, vestibular, proprioceptive, tactile, olfactory and gustatory, and other parts of the somatosensory system, in connection with the peripheral retinal fibers.

The retina has approximately one million sensory receptors in each eye. These retinal sensors convert light into electrical impulses that travel through the optic nerve, the optic chiasm and the optic radiations. 80% of the light—the retinal input—goes through the lateral geniculate nucleus (LGN) at which point it combines with signals from other sensory systems. Thus, this visual and non-visual fiber information combines with auditory, proprioceptive, vestibular and other sensory signals. The other 20% of the retinal input is split so that some of it goes to the limbic system instead of through the LGN, while the rest of it goes to the pretectal area, the superior colliculi and the accessory optic system. It is on these areas where the punctal or lacrimal plugs and other filtering devices, which alter the angle and input of light, have an original effect, which then interacts at the sensory associative cortex (posterior parietal cortex), with the 80% that went through the LGN. There are feedback loops throughout the connective systems. Therefore, by controlling the amount and angle of light in different directions, you can intentionally stimulate or not stimulate specific retinal receptors. By using only standard lenses wherein light is directed only to the central parts of the eye, then the peripheral parts and all of their symptoms are excluded from diagnosis and treatment.

Persons with mismatched sensory systems can benefit from treatments using one or more of the methods of the present invention. These treatments can lead to an integration of sensory inputs, which can have a positive effect on all forms of learning and performance.

Via retinal connections in the retinohypothalamic pathway, mood disorders, such as depression, anxiety, sleep disorders, stomach disorders and motion sickness can be partially addressed by calming the nervous system and creating a greater flexibility in range of motion of muscles, and hip and neck stability. Changing the tear layer alters stimulation of the trigeminal nerve, which can impact on people with trigeminal neuralgia. Because the temporal or other cranial bones may be shifting after insertion of the punctal plugs, Temporomandibular Joint (TMJ) disorders can be evaluated or improved. Moreover, it is known that tears contain a variety of hormones and neurotransmitters. Thus, an alteration in the volume of tears in the eye can be used as a natural hormone treatment. This effect can also be useful in the treatment of sleeping disorders, motion sickness and elevated intraocular pressure as occurs in patients with glaucoma.

Other benefits are realized also. For example, the impact in basic tasks such as paperwork is complemented and improved upon. Improvement can also be realized in a variety of other areas including, but not limited to, attention, concentration, cognition, creativity, articulation, expressive and receptive language, handwriting, reading fluency of both words and music, reading comprehension, sensory integration, eye movement control, improved note taking in classroom situations, improved performance in sports (including reaction time and coordination). Auditory localization ability is enhanced, as is motor control and motor planning of both gross and fine muscles at both reflexive and cortical levels, respectively. Additional benefits include improved hearing of musical pitch, timbre, rhythm, volume and frequency. For example, people receiving the treatments can hear a change in the speed of entering sounds (i.e. teachers may appear to be speaking more slowly or their voices will not appear to fade in and out).

A person receiving one or more of the treatments can also realize improvement in increased energy, less eye strain and muscle relaxation due to the enhancement of thickened tear layer which reflects light uniformly on the peripheral retina, acting as though it were a lens and improving visual performance. Persons using the punctal or lacrimal plugs or one or more of the other treatments and methods of the present invention experience stabilized balance, alteration of tinnitus, vertigo and enhanced spatial orientation and organization. The increased moisture on the cornea affects the sense of balance via the various linkages among the vestibular, proprioceptive, visual and auditory magnocellular pathways, thus affecting spatial orientation.

The methods of altering retinal input has usefulness for people on the entire autistic spectrum, including people with dyslexia and speech and motor delays. Also there can be limited positive effects on balance and mobility issues by altering sensory integration in patients with neurological and muscular impairment, either congenital or acquired, such as with Traumatic Brain Injuries (TBIs),along with progressive neurological disorders such as Alzheimers', Parkinson's Disease, Cerebral Palsy, Down Syndrome, Multiple Sclerosis and Muscular Dystrophy. Also seizure disorders can be affected by changing visual and non-visual retinal signals. Further, such treatments will be useful in treating phantom limb pain in individuals who have lost limbs.

Additional features and advantages are described herein, and will be apparent from the following Detailed Description and the figures.

BRIEF DESCRIPTION OF THE FIGURES

FIG. 7B shows one embodiment of a sensory organization test's center of gravity (COG) tracing;

FIG. 7C shows one embodiment of a sensory organization test chart;

FIG. 7D shows one embodiment of a sensory organization test chart and graph;

FIG. 7E shows one embodiment of a sensory organization test's center of gravity (COG) tracing;

FIG. 7G shows one embodiment of a sensory organization test chart;

FIG. 7I shows one embodiment of an adaptation test chart;

FIG. 7L shows one embodiment of motor control test average data;

FIG. 7M shows one embodiment of a motor control test chart;

FIG. 7N shows one embodiment of sensory organization test results;

FIG. 7O shows one embodiment of sensory organization test results;

FIG. 7P shows one embodiment of a sensory organization test's center of gravity (COG) tracing;

FIG. 7Q shows one embodiment of sensory organization test raw data results;

FIG. 7R shows one embodiment of sensory organization test results;

FIG. 8 shows one embodiment of the Zelinsky Intervention Response Chart;

FIG. 10 shows one embodiment of the Z-Bell Test Scoring (Auditory and Visual) chart.

DETAILED DESCRIPTION

Figure 1:
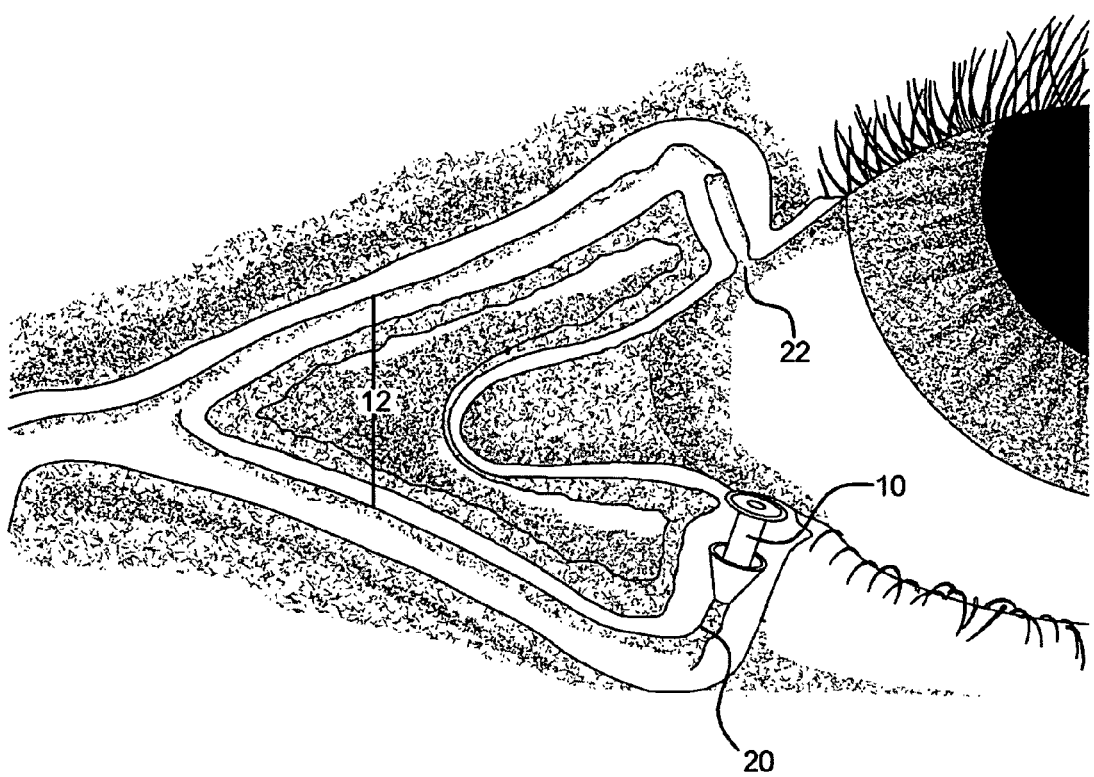
FIG. 1 shows a cross-sectional view of a portion of a person's lacrimal system with one embodiment of a non-dissolvable silicone plug inserted in the lower punctum.

While the present inventions are susceptible to embodiments in various forms, there is shown in the drawings and will hereinafter be described some exemplary and non-limiting embodiments, with the understanding that the present disclosure is to be considered an exemplification for the invention and is not intended to limit the invention to the specific embodiments illustrated. In this disclosure, the use of the disjunctive is intended to include the conjunctive. The use of the definite article or indefinite article is not intended to indicate cardinality. In particular, a reference to "the" object or "a" object is intended to denote also one of a possible plurality of such objects.

One embodiment relates to methods for diagnosis and treatment of processing difficulties, integration problems and imbalances through the Z-Bell Test, modification of eye moisture and light-eye interaction using various treatments and interventions including the use of punctal or lacrimal plugs (or any surgical or non-surgical partial or total blockage or closure of the lacrimal system), opaque or colored or non-colored contact lenses, translucent or enhancer tinted contact lenses, visible tint contact lenses, eyeglass lenses with or without tints or filters or prisms, occluders, neutral density or other types of filters, partial or total light blocks, prisms, tear dye, partial or total blocking of light to the eye, i.e. visors or other types of non-lacrimal occluders, blinders, filters, and/or modification of head position, posture and/or muscle tension.

Figure 2:
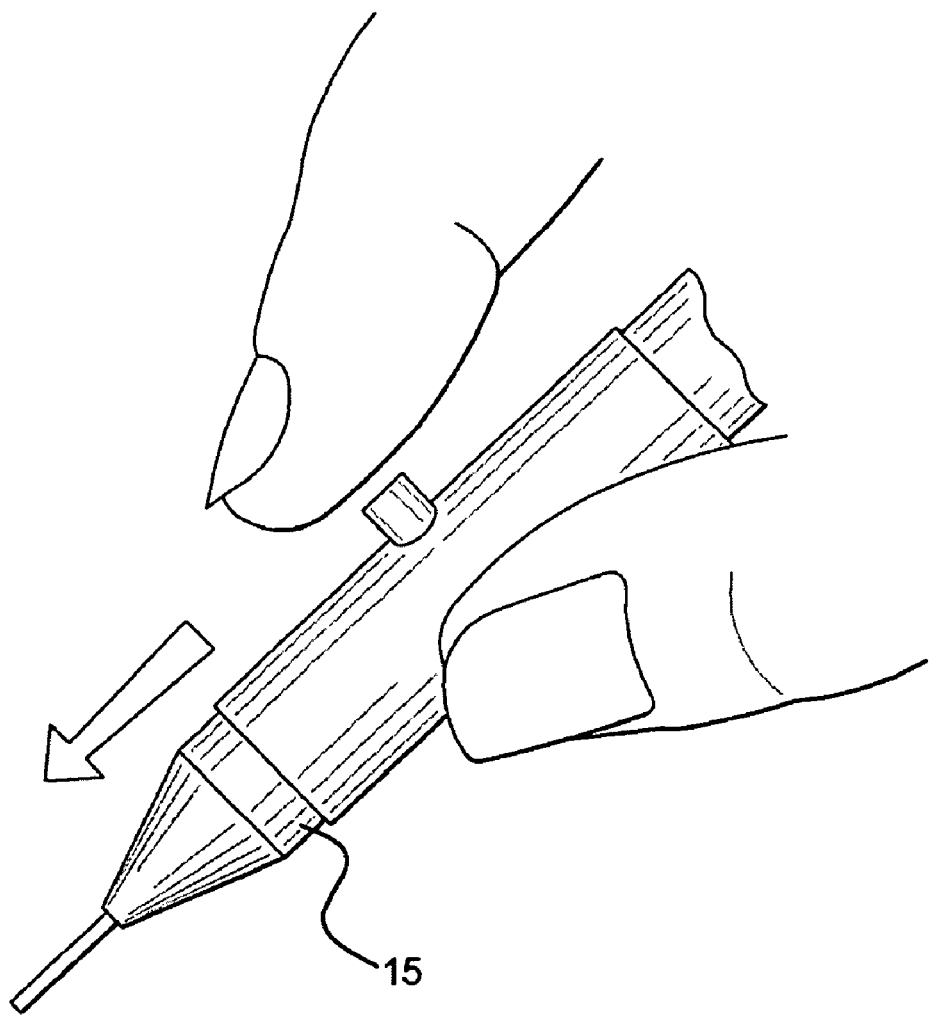
FIG. 2 shows one embodiment of a plug inserter.

As shown in FIG. 1, the eyelid contains two holes called a lower 20 and upper 22 punctum which are, parts of the lacrimal drainage system. FIGS. 1 and 2 show one brand and type of punctal plug 10 and inserter 15 from Odyssey Medical, Inc. that can be used for multiple applications of the methods. Other brands and types of configurations of plugs and inserters may also be used. The plugs are designed to be inserted into and plug the lacrimal drainage system in each eye. In most cases, the methods described herein use the standard procedures that the plug manufacturer recommends for these particular applications of plugging the lower and/or upper puncta. The entire system is not closed off because only one punctum is plugged; i.e., if only the lower punctum is closed, there is also a punctum in the top eyelid and the two puncta both drain tears and feed into a sinus. The original intended use of these plugs is to work with post-nasal drip, sinus problems and dry eyes.

The theory of operation of the plugs 10 rests in part on the fact that the sinus accumulates and accepts matter from the ears, eyes and throat. If the tears that are flowing to the sinus are stopped by plugging the lower puncta 20, then the body can more easily handle the remaining fluid from the ears and throat. For some applications, manufacturers often suggest first using a collagen or a dissolvable plug as a trial for patients having dry eyes. The dissolvable plugs last for about 7-8 days and then an observation is made to determine if the patient's symptoms go away and then recur when the plug dissolves. If the symptoms reappear, then a more permanent silicon plug 10 is used. For most of the novel methods disclosed herein, a permanent silicon plug is used so the doctor can remove it quickly if a problem is detected. The dissolvable plugs are considerably more difficult to remove than the permanent plugs 10.

Figure 3:
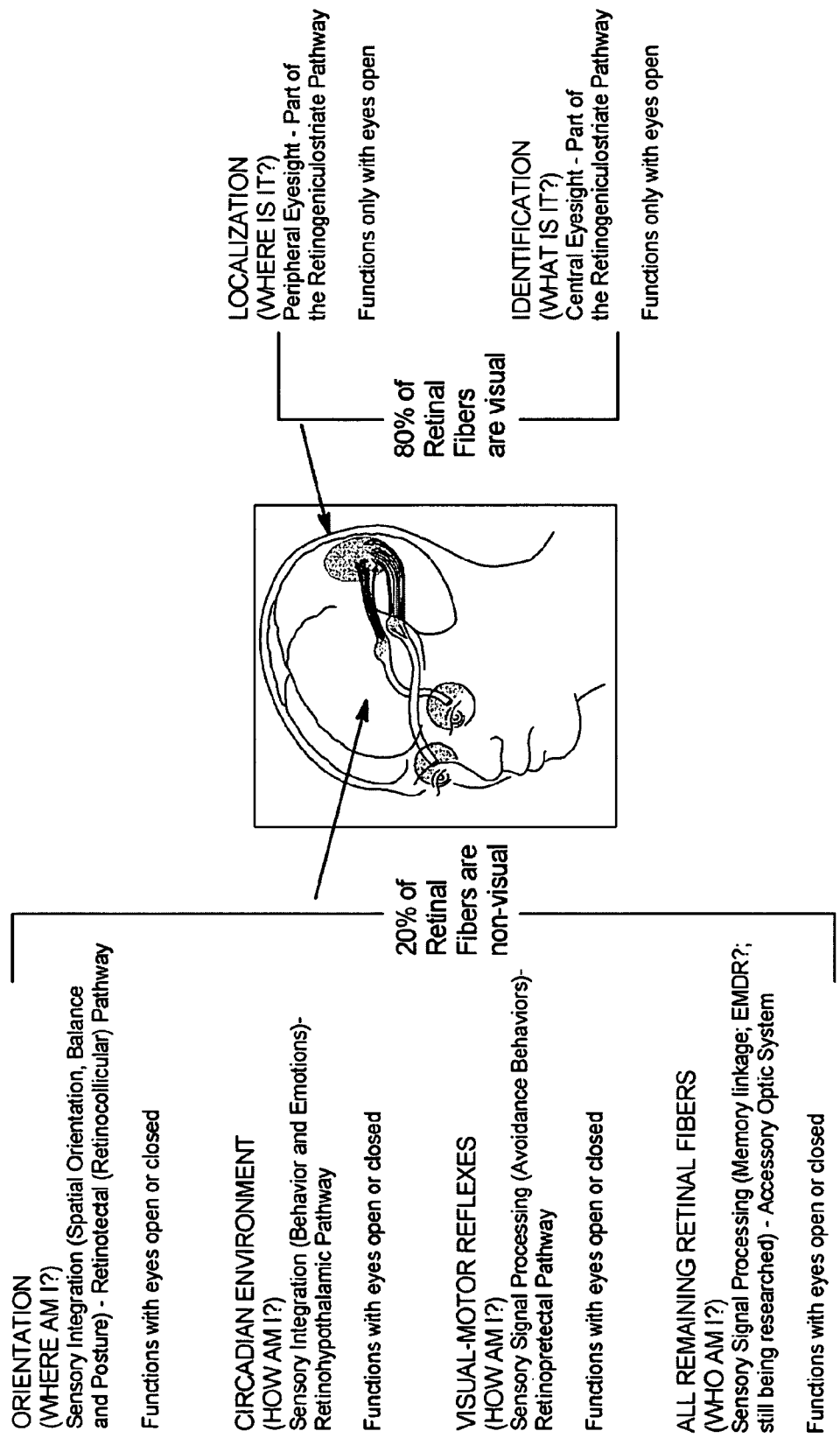
FIG. 3 shows one embodiment of a perspective view generally of a person's retinal processing pathways.
Figure 4:
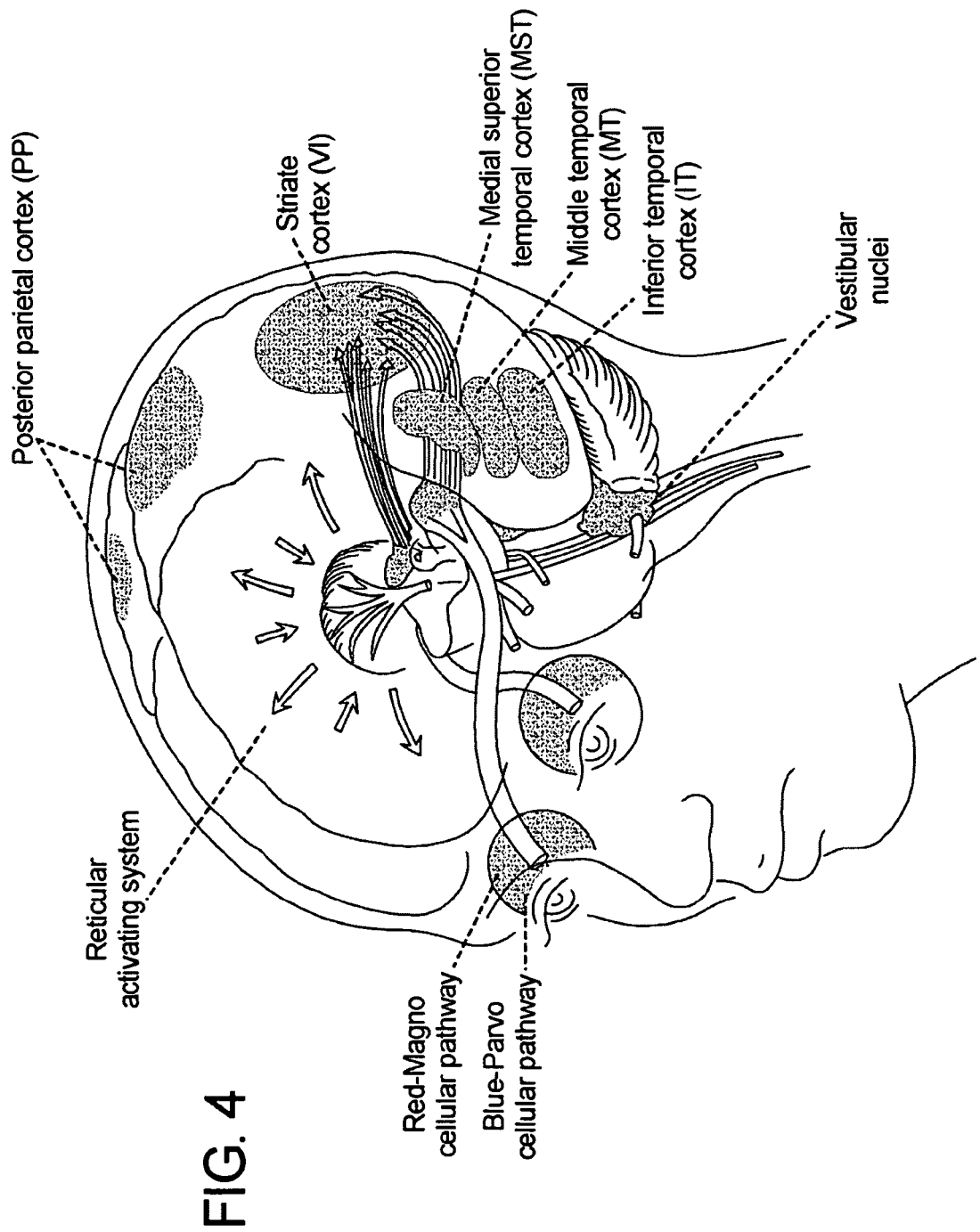
FIG. 4 shows one embodiment of a perspective view generally of a person's central and peripheral retinal connections to the brainstem, limbic system and cortex.

There are approximately 160,000 retinal fibers per eye that are not connected directly with eyesight. See for example FIGS. 3 and 4. These non-visual fibers transmit signals that link, via the midbrain, tectum, limbic system and lateral geniculate body, with other sensory signals. In patients with processing disorders, sensory integration disorders, abnormal postures or biochemical disorders, the alteration of the entering light on the retina affects sensory linkages. The amount of moisture on the eye affects the bending of light onto the retina. When the eye is dry, the tear film on the surface of the eye is not uniformly smooth, so the light does not always get bent in the proper way, and visual distortion occurs. By allowing the tears to stay in the eye longer, the tear feedback mechanism enables the brain to register an increased amount of tears, and assume that the person is relaxed. When a patient is agitated, certain hormones are produced in the body, including the tears. When the person is relaxed, they produce different hormones. Alteration of the tear layer affects the hormone levels in the tears, and will change the signals in the feedback and feedforward mechanisms. Eyes get drier when subjected to stressful conditions; blink rate is diminished, tear production is lessened.

A novel principal of operation of these methods relies in part on the unexpected discovery that bending of the light and alteration of the tear film in patients who do not exhibit dry eyes difficulty still has a profound effect on other difficulties the patient is experiencing. These novel methods do not require that the patient be diagnosed with insufficient tear film. The uniformity of the tears does much more than simply moisten the corneal surface. These methods of altering light-eye interaction described herein provide a novel, beneficial and useful alteration to the linkages between auditory, visual, vestibular, proprioceptive, tactile, olfactory and gustatory, and other parts of the somatosensory system pathways at both a subcortical (reflexive) and cortical (non-reflexive) level. The alteration of light and tear layer is also useful in the diagnosis and/or treatment of certain symptoms and/or processing and integration difficulties for patients of all ages. Such processing difficulties include, but are not limited to, dyslexia, motion sickness, attention and concentration problems, learning disabilities, balance disorders and/or posture imbalances (including midline shifts), post-traumatic stress syndrome and vestibular dysfunctions such as vertigo. Even electrical trauma survivors benefit from the alteration of their tear layer.

The retina has more than one million receptors in each eye. They are mapped so that when light triggers them the light is changed into electrical impulses traveling through the optic nerve and the optic chiasm. About 80% of the light goes through the lateral geniculate nucleus (LGN) at which point it combines with light from other senses. At the LGN the visual fiber information combines with auditory, vestibular, proprioceptive, tactile, olfactory and gustatory, and other parts of the somatosensory system. This accounts for 80% of the retina input. The other 20% of the retina input is split. Some of it goes to the emotional centers in the brain, the limbic system. As such, it doesn't go through the LGN. Other parts of it go straight to the superior colliculi and deal with spatial orientation, on which filtering devices and the punctal plugs have an effect. In summary, 18% goes to the superior colliculi, tectum and pretectum, and accessory optic pathway, 2% goes via the retinohypothalamic pathway into the limbic system and 80% goes to the LGN.

Under normal circumstances there are feedback loops between all the sensory systems at both cortical and subcortical levels. When there is a sensory integration disorder, these feedback loops are also affected. An intervention using the methods of this invention can restore integration, and thereby the feedback loops, which are essential for normal body function. Via the retinohypothalamic and the retinopretectal pathways, these feedback loops also have an effect on the parasympathetic nervous system and on psychological well being, specifically on psychological disorders and issues of anxiety and depression. Altering retinal input has usefulness for people on the entire autistic spectrum, including people with dyslexia and speech and motor delays. Also, there can be limited positive effects on balance and mobility issues by altering sensory integration in patients with neurological and muscular impairment, either congenital or acquired. Lenses only (as prescribed by standard eyecare professionals) bend light on the central parts of the retina and its surrounding space. Both visual and non-visual peripheral retinal receptors are not often considered in an evaluation. Therefore, many symptoms arising from the peripheral retinal connections are being ignored.

One way to determine stability of sensory integration and retinal receptor sensitivity is by using the Z-Bell Test, which is a method of the present invention. The test can also be used to evaluate the presence of residual primitive reflexes by observing whether the patient isolates his shoulder muscles from his neck and eyes when he reaches for the target. During the Z-Bell Test, if a person with eyes closed can locate the sound, he has tested normal and if he cannot, there is a spatial orientation and sensory integration problem. This test involves the stimulation of visual and non-visual retinal sensors and their linkages at both cortical and subcortical levels. In a normal patient, whose spatial orientation is not fragile and where sensory processing is correctly linked, a distortion of retinal input (via a lens, prism, filter, colored tint or insertion of plugs to partially or totally block the lacrimal drainage system) will also create a corresponding distortion of the auditory information and this patient will then be disoriented and inaccurately reach for the bell. In patients whose spatial orientation is fragile, where auditory and visual pathways are not solidly integrated, if the same intervening factor is introduced, there is not a distortion in auditory localization, as it should be. Thus, the patient with impaired spatial orientation and sensory integration will accurately reach for the bell. In other words, altering the retinal input will disorient the normally functioning patient, but not patients with impaired integration, unless they shift their posture to accommodate to the distortion.

In one form and application, the "Z Bell Test" used to determine the stability of sensory integration, retinal receptor sensitivity and for evaluation of the presence of residual reflexes are other novel. In one embodiment, the Z-Bell Test has two components: auditory and visual localization. Generally, in the auditory localization task, the patient closes his eyes and is asked to localize a sound in front of him by touching the ringing bell with one finger. In other embodiments of the invention, other sound generating devices may be substituted for the bell. Generally, in the visual localization task, the patient is asked to look at a nonmoving target in a small space, close his eyes, and then reach for the target with one finger. Sometimes a patient cannot find the bell at all, indicating poor sensory linkages. However, in most cases, after the plugs 10 are inserted he can instantly find the bell. The ability to accurately localize the sound of the bell represents, for example, the ability to hear a teacher in a noisy classroom. This linkage of auditory signals with other sensory systems can also provide enhanced auditory feedback necessary for clear articulation. Then, three months later, for example, when the same patient returns to have the plugs removed, his own auditory feedback systems and sensory integration is working and the presence of the plugs becomes a hindrance and he is only able to accurately find the bell after removal of the plugs, indicating that the plugs altered his spatial orientation. During testing, bells with different frequencies have been used and it is discovered that, for example, one frequency (the musical tone A) in particular is very easy for children with attention deficit disorder to find and other frequencies are not as easy for them to locate. The children who exhibit these problems when their neck position changes, or when the frequency of the sound changes, are not able to integrate sounds and sights. New research on dyslexia has shown how sounds and sights need to link together and that they are not linking properly in dyslexic children. After insertion of the plugs, some types of dyslexia are eliminated. By inserting the plugs in the children, the benefit experienced is the linking of sights with the memory of phonetic sounds and therefore the children are reading better and some types of dyslexia are eliminated.

In one form of the Z-Bell Test, the test evaluates one aspect of auditory/visuo-spatial organization and how it is affected by changes in light and posture. Visual and posture changes have a direct bearing on the information transmitted at the midbrain via the auditory, visual, vestibular, proprioceptive, and motor pathways. The mind is confused by sensory mismatches and tries to compensate. The Z-Bell Test can detect a mismatch in spatial organization and allows the doctor to use this additional diagnostic tool in formulating remedial or compensatory treatment. The Z-Bell Test also serves as a powerful demonstration tool.

The following explains more specifically how the Z-Bell Test works. The mind readjusts perceived auditory location when perceived visual location is shifted. It tries to avoid a visual-auditory mismatch through the dominant visuo-spatial perception. If visuo-spatial perception does not dominate, a sensory integration dysfunction is indicated.

For example: (1) a bell is rung three feet directly in front of a patient. He both sees and hears it as located three feet in front of him; and (2) prisms are placed on the patient so that he now sees the bell as one foot to the right. The bell is actually still located at midline (directly in front of him). When the bell is rung, and he is asked where the sound is coming from, he responds, "Approximately one foot to the right." This mental readjustment also occurs even with the eyes closed. Examples of various embodiments of the Z-Bell Test follow. Variations of the steps of each embodiment are also possible and within the scope of the multiple present embodiments.

Z-Bell Test: AUDITORY

1. Have a seated patient close his eyes.
2. Select a location within the right test zone (see FIG. 10), an area between the shoulders, above the armpits, no more than four inches above the head and approximately 12 to 16 inches (Harmon distance) in front of him. Avoid midline as a test location.
3. Remind the patient to keep his eyes closed, and ring the bell at the selected location.
4. Ask the patient to touch the bell with his forefinger.
5. Score the test, using the Accuracy Scale as shown in FIG. 10.
6. Repeat steps 3 to 5, ringing the bell in the left test zone.

Z-Bell Test: VISUAL

1. Have the seated patient open his eyes and put his hands at his sides.
2. Point the bell handle toward him, using the same right test zone as in the Auditory test.
3. Ask him to close his eyes and visualize the bell handle.
4. With his eyes closed have him try to grasp the tip of the bell handle with his thumb and forefinger. Allow him to choose which hand to use.
5. Score the test, using the Accuracy Scale as shown in FIG. 10.
6. Repeat steps 2 through 5, in the left test zone.

Figure 9:
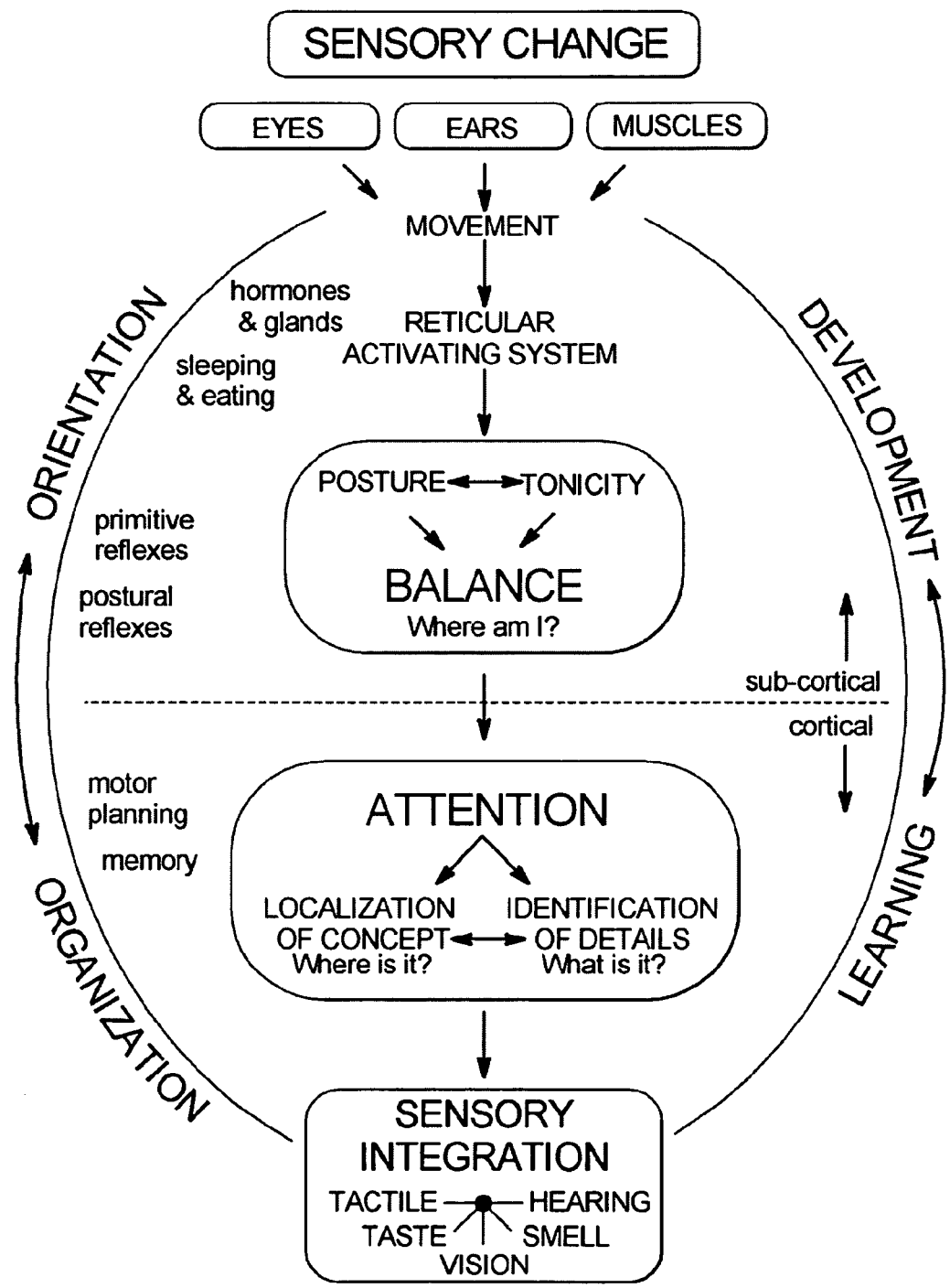
FIG. 9 shows one embodiment of components of sensory integration chart.

In one embodiment, a novel principal of operation of the Z-Bell Test is the unexpected discovery that the test can determine the stability of sensory integration and retinal receptor sensitivity and can evaluate the presence of some residual primitive reflexes. Other unexpected and novel discoveries are that the Z-Bell Test includes both aspects of retinal transmission, see FIG. 3; the auditory part diagnoses sensory linkages of the non-visual fibers and the visual part diagnoses spatial perception with the visual fibers. See also generally FIGS. 4 and 9. In one form, the Z-Bell Test was originally developed solely to aid in the choice of proper lens prescription and as a way to demonstrate to optometrists how auditory localization could be altered by changing visual input through a closed eyelid.

Since its inception, yet additional novel uses of the Z-Bell Test have been discovered that have expanded its applications beyond its original auditory format and even the range of sound used during testing has been expanded. By including in the Z-Bell Test a wide range of frequencies, the doctor is able to determine which patients are able to localize many frequencies of sound and which patients are able to localize only one or two. Therefore, the flexibility of spatial orientation and the tolerance range of stray light can be evaluated. Also, simply by observing the manner in which the patient attempts to reach for the various sound locations during the test, the doctor can isolate the neck, shoulder and eye movements and determine the presence of some primitive reflexes. By performing the test while the patient is standing the doctor can examine all sensory linkages by varying posture, weight bearing and lighting during the test. It was also discovered that an evaluation of the autonomic verses the central nervous systems can be made by a refinement of the application of blinders, visors, punctual plugs, yoked and non-yoked prisms and tints, or a combination of the above, within the framework of the new Z-Bell Test protocols. Also, additional research indicates that the Z-Bell Test can evaluate a patient's preferred auditory and visual frequencies and their correlation with each other.

One form is a novel method of diagnosis and/or treatment of various processing difficulties, integration problems and imbalances by the alteration of the nervous system through treatment and the use of aids such as punctal or lacrimal plugs 10. As is known in the prior art, and described above, the plugs are commonly used for the treatment of dry eye syndrome. They work by maintaining moisture on the front surface of a dry eye and are not known to be used for diagnosis and treatment of processing difficulties, integration problems, posture and balance disorders and biochemical imbalances.

During patient evaluation, the doctor makes observations to determine if the patient may require one of the herein described novel methods of treatment employing punctal or lacrimal plugs. Following are examples of some potential symptoms a doctor may observe. Even if a patient has 20/20 eyesight in each eye and does not need glasses to improve his vision, the patient may be experiencing motion sickness, problems with balance, poor attention span and/or poor reading ability because his eyes jump around on a page when reading. Some of the patients convey that they see floating words when they are reading, which usually indicates that the central eyesight and the peripheral vision are not properly linking together. Other observations that may indicate that the plugs should be inserted in the patient are people who exhibit, for example, autistic spectrum tendencies, speech delays, motor delays, neurological impairment or who are diagnosed with Traumatic Brain Injuries (TBIs), Parkinson's Disease, Cerebral Palsy, Down Syndrome, Multiple Sclerosis, Muscular Dystrophy, Alzheimer's Disease, seizure disorders, trigeminal neuralgia, sleep disorders, Temporomandibular Joint (TMJ) problem, emotional (mood) disorders or gastrointestinal disorders. Insertion of the plugs may also help the professional performance of, for example, musicians, aviators, navigators, athletes, academics or linguists by restoring or enhancing sensory linkages and reestablishing the neuromuscular control in the body via retinal connections in the retinohypothalamic, retinopretectal, retinotectal and accessory optic pathways. Changing the tear layer alters stimulation of the trigeminal nerve, which can impact on people with trigeminal neuralgia. Because the temporal or other cranial bones may be shifting after insertion of the punctal or lacrimal plugs, TMJ disorders can be altered.

One technique included in methods for evaluating sensory linkage deficiencies and as a part of determining if the novel methods of using the plugs, or other methods of partial or total lacrimal blocking, for treatment is required is the usage of a questionnaire. The following are some examples of questions that a doctor might ask a patient: Do you have frequent neck/shoulder muscle tension? Can you wink each eye? Do you have lower back problems? Can you study easily with background noise? Can you sing on key when placed next to someone singing a different melody? If you are absorbed in a project, do you forget to eat? Do you take people's words literally (as opposed to "reading between the lines")? Do you have a good sense of balance? Do you have a good sense of rhythm? Do you play music by ear?

After insertion of the punctal plugs and increasing the patient's tear level, for example, a patient who experienced motion sickness will no longer exhibit that symptom. Further, patients usually experience more acute hearing and they can keep up with auditory input more quickly with less effort. Also, insertion of plugs into the puncta ultimately affects sensory integration, spatial orientation and spatial localization abilities, which are the foundation for posture, attention span, learning, organization, focusing ability, etc. The plugs are used to alter the linkages between auditory, visual, vestibular, proprioceptive and other sensory pathways at both a reflexive (brainstem) and cortical level (including feedback systems involving the cerebellum). Plugging or occluding one or more of the tear ducts may be complete or partial and may be accomplished not only with punctal or lacrimal plugs, but also through the use of surgery or other interventions. Additionally, insertion of the plugs can impact the linkage between auditory and visual processing as well as the linkage between postural control and balance as exhibited in patients with retained primitive reflexes. By plugging the tear ducts and creating more tear moisture and thereby more hormones which are carried in the tears, the patient usually immediately feels much better and his symptoms are often immediately eliminated or lessened.

Figure 5:
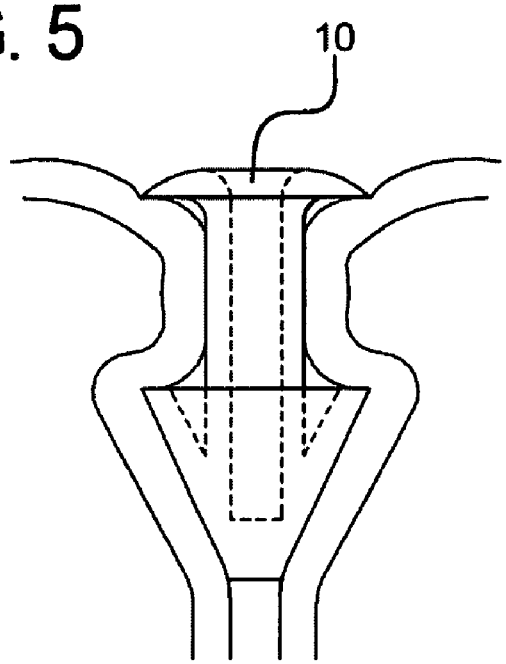
FIG. 5 shows a partial cross-sectional view of one embodiment of a plug inserted in a person's punctum.

Once the plugs 10 are inserted into a patient using an inserter 15, the patient will remain in the doctor's office for about 10 minutes to confirm the plugs are not bothersome. FIGS. 1 and 5 show plug 10 inserted in a patient. Common sensations a patient might temporarily experience are minimal, and might include minor changes in other sensory systems and/or a slight pressure in his lacrimal drainage system. If the patient experiences some scratchiness then the plug is lightly tapped downward until the patient feels more comfortable.

Figure 6:
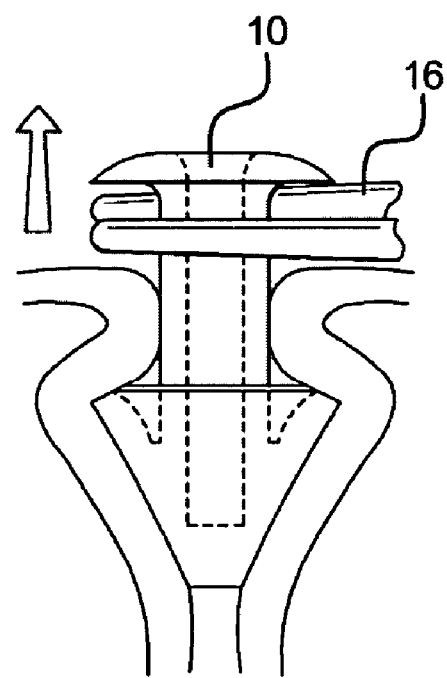
FIG. 6 shows a partial cross-sectional view of one embodiment of a plug being removed from a person's punctum.

Under manufacturer's recommended standard of care the plugs would be set for two years whereas under one application of the herein described methods, the plugs will be removed from the patient in approximately four months. It can take up to seventy-two hours for the upper puncta to reorient themselves to accommodate the added tear flow. Patients may visit the doctor at intermediate periods while the plugs are positioned in the puncta so the doctor can re-test and compare the findings from the first tests and make changes if required. It may take approximately three months until a patient has actually experienced a more permanent change in his tear physiology. At that time the plugs are removed and in many cases the patient's tear physiology has changed so the patient continues to receive the benefits of the changes. FIG. 6 shows removal of plug 10 using a removal tool 16.

In yet other forms, a lacrimal plug can be used which inserts into the canaliculi 12. See FIG. 1. In other applications, the puncta can be sewn closed. For yet other applications, partial flow plugs may be used because for certain patients the size of the plugs and amount of additional tear flow produced creates various different benefits and produces different effects.

By using the novel methods involving plugs 10 and eye tear level manipulation as described herein, some of the following benefits may be experienced by patients, for example: improvements to balance, vestibular problems, vertigo, motion sickness, attention and concentration (focusing ability), depression, anxiety, enhanced spatial orientation, spatial organization, posture, energy level, eye strain, the auditory system, articulation, expressive and receptive language, speech, auditory localization, hearing of musical pitch, timbre, rhythm, volume, frequency, apparent speed of sounds, tinnitus, learning languages, learning disabilities, handwriting, reading fluency for words and music, reading comprehension, eye movement control, sensory integration, note taking, cognition, creativity, memory, motor coordination, sports performance (reaction time, coordination), primitive reflex integration, motor control and motor planning of gross and fine motor muscles at both subcortical (reflexive) and cortical (conscious and subconscious) levels and muscle tonicity.

After wearing plugs 10, patients have been tested using standard optometric tests. An example of the positive results of some of those tests and the different conditions has shown that, for example, patients exhibit changes in that they can more successfully aim their eyes, point to a target and follow a moving target. Some patients don't experience any of those types of changes but will experience less of a fatigue factor or they will experience better attention and concentration ability.

After use of plugs 10, some of the patients also experience that their motion sickness has disappeared when they travel in trains, airplanes and cars. Patients experience that their auditory system is better and that they hear more sharply. Children experience that their teachers seem to be talking more slowly thereby making it easier for the children to understand and process the information. Adults experience that they hear better in meetings and that they think better and more clearly. Phone salesmen experience that they can hear on the phone more easily and understand their clients much better. Certain patients experience that neck problems are eliminated or reduced in severity. Children's reading and comprehension levels have shown improvement. Several children have improved their reading skills up to more than two level/years. One patient who had been in gymnastics two times a week for years and couldn't get to the next level of difficulty because she couldn't perform a certain type of cartwheel was able to finally achieve the cartwheel and qualify for the next level after a single treatment with the plugs.

Figure 7A:
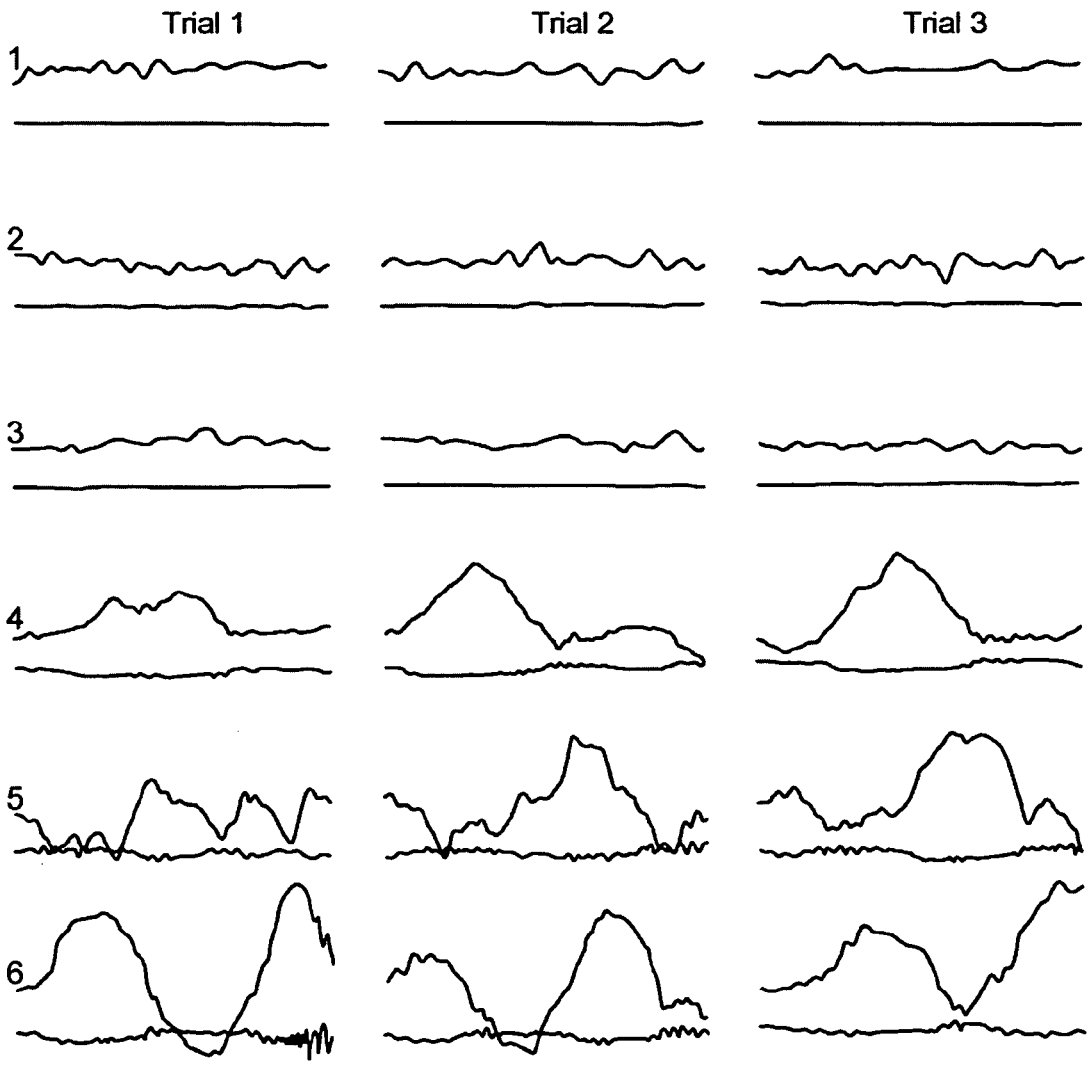
FIG. 7A shows one embodiment of a sensory organization test raw data chart.
Figure 7F:
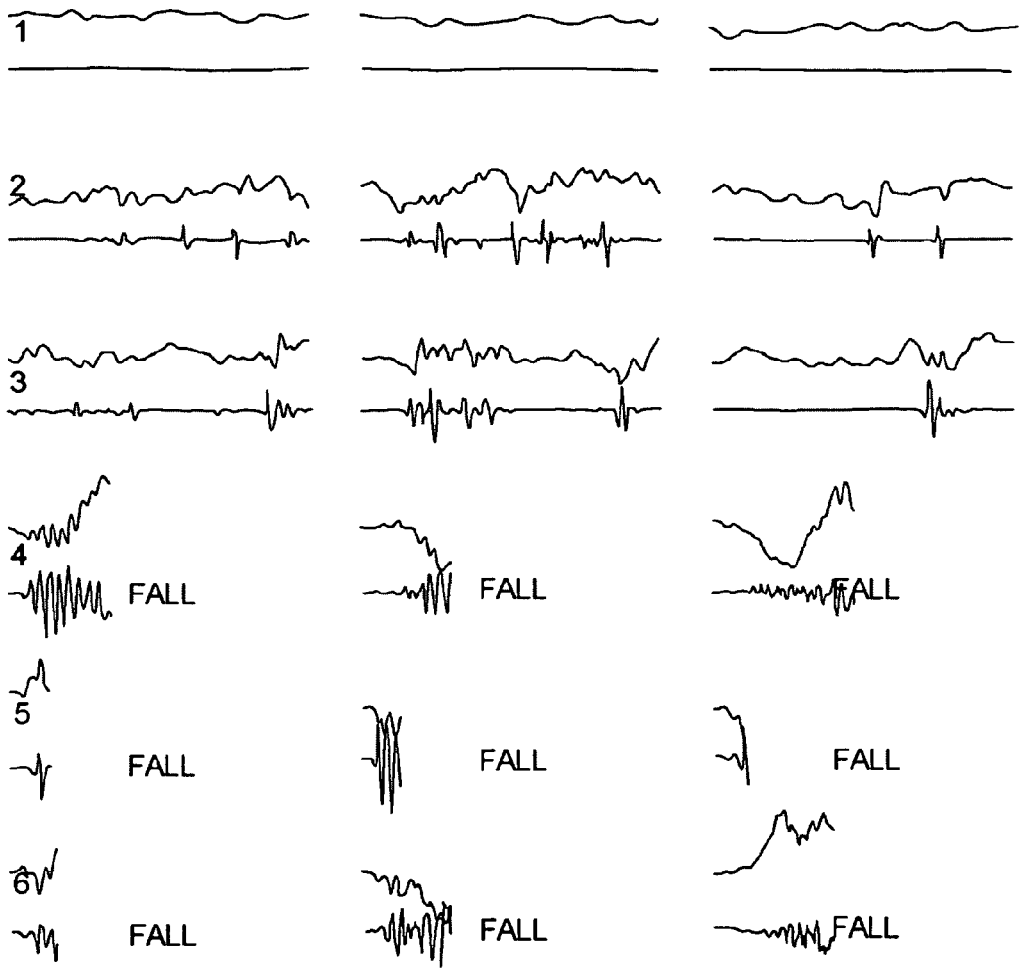
FIG. 7F shows one embodiment of a sensory organization test raw data chart.
Figure 7H:
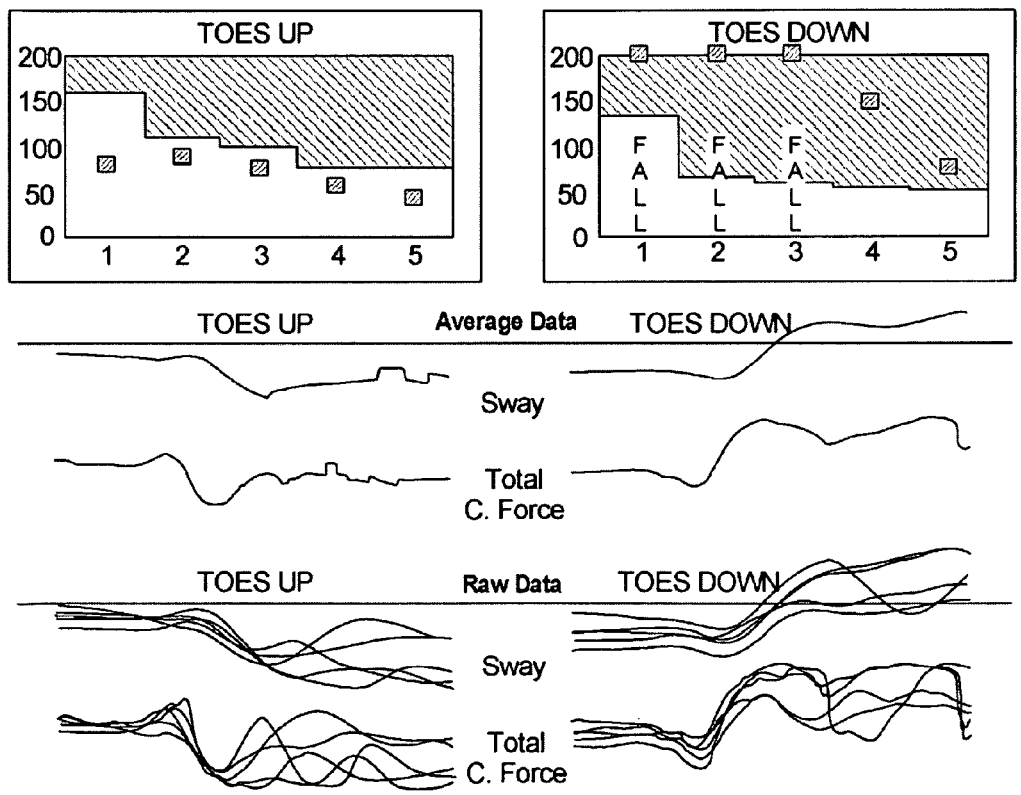
FIG. 7H shows one embodiment of adaptation test graphs and traces.
Figure 7J:
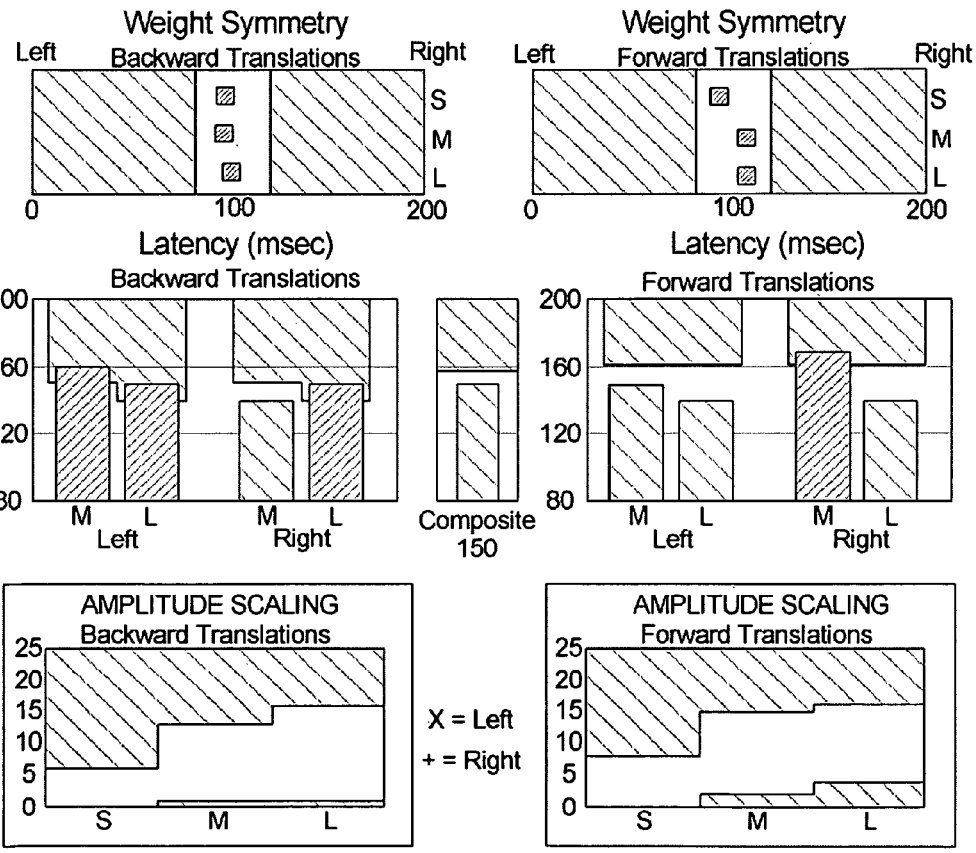
FIG. 7J shows one embodiment of motor control test results.
Figure 7K:
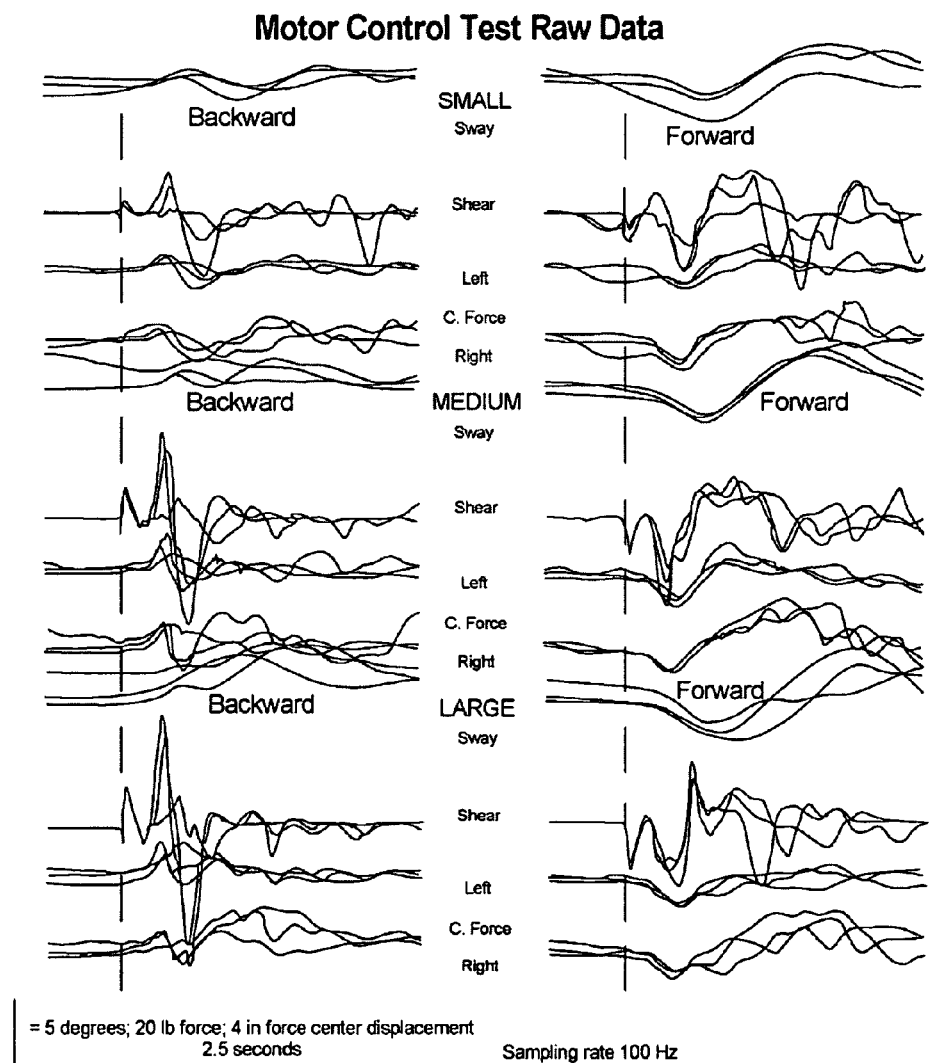
FIG. 7K shows one embodiment of motor control test raw data.

Attached as FIGS. 7A-7R are examples of a sensory organization test and examples of the charts from the different test readings for the following experimental example. The figures demonstrate how after blockage of the lacrimal system by insertion of a punctal plug, a significant and immediate change in balance and sensory organization at an unconscious level was measured. This documentation demonstrates how non-visual retinal signals directly affect other sensory systems and body posture. The tests were performed using a balance machine to test equilibrium in patients and separate the concept of balance into visual, vestibular or somatosensory contributions. The visual system is but one part contributing to a person's balance. The inner ear (vestibular), auditory and proprioceptors are other parts of balancing. This sensory organization test has six conditions. The first two conditions require the patient to stand with his feet on sensors, eyes open and eyes closed, respectively. The following two tests have the surrounding visual environment and the floor move, respectively, with the patient's eyes open. The fifth condition has the floor move with the patient's eyes closed, and the sixth and hardest condition has the visual surroundings and the floor moving at the same time. Measurements of whether the patient regains his balance after being disoriented by leading with his ankles or his hips is measured by virtue of sensors under his toes and heels. The sensory organization test provides three trials for each of the six conditions.

This test example used a patient who had developed a brain abscess which had damaged her cerebellum, her temporal lobes and some parts of her parietal lobes. She experienced significant difficulty with balance and walking. She also had a history of seizures. During the above sensory organization test for equilibrium, the patient was unable to handle the conditions when the reference around her was moving and she kept losing her balance because she couldn't shift her weight by using her ankles or hips quickly enough to reorient. During the test, the ankle and hip reactions are measured by sensors under the feet. The tests measure how much a person requires his eyes to keep balance, how much the inner ear is used and how the person uses proprioception. This patient wasn't able to effectively use either her visual or her vestibular system and relied instead almost solely on somatosensory input. The patient attended physical therapy for two months. Then she redid the same tests and the results were almost identical. The center of gravity was a little better and the strategy analysis of how she used her hips was a little better. The tests still showed that if the floor were tipped downwards she would fall over. She was not able to react and push her body backward when the floor tipped downwards.

Using the novel methods, tear plugs 10 were then inserted in her puncta. Fifteen minutes after the insertion of tear plugs she was retested on the balance machine and the results for the sensory analysis showed that she used all three measured systems almost normally and was able to maintain her balance, even during the most difficult condition when both the surrounding visual input and platform under her feet were moving simultaneously. The test findings went from minimal usage of visual and vestibular information to almost normal usage. The strategy analysis part of the test showed normal strategy. The center of gravity alignment was nearly perfect. Very little swaying was exhibited and on the sixth test condition, which is the most difficult, where the patient had her eyes open and the reference and her feet were both moving. Her learning curve showed that she was improving significantly. Once the tear plugs were inserted, two of the test results became better than normal and one of the results showed a learning curve improving within minutes. There also was an instant change in her auditory awareness as measured by the Z-Bell Test.

By partial or total blockage of the lacrimal system using the novel methods, the auditory and motor feedback is changed. A patient with articulation problems experienced immediate improvement. This fourth grader had been in speech therapy since first grade. After insertion of punctal plugs in his lower puncta, his rhythm, speech and reading all improved. In the mid-brain there are fibers from the retina that go to the superior collicula that also link with the inferior colliculus of the auditory center. At the tentorium, which is where the inferior and superior colliculus link, after insertion of the punctal plugs, the synchronization of auditory and visual signals became more stable and less likely to be disrupted. Changing spatial orientation and organization with the invention also affects receptive and expressive language. Auditory details were able to be isolated from background noises in another patient.

In yet other patients, problems of anxiety, depression, concentration and attention showed a significant positive effect after using the novel methods of the present invention. Their sense of anxiety and depression was lessened and there were improvements in concentration and attention. Balance and walking abilities showed improvement as did neck and posture problems. In several cases, patients who specifically couldn't read in a car without experiencing motion sickness were able to do so after punctal plugs were inserted. Neck tension and shoulder tension can change and improve. In yet other situations, where a person cannot sit comfortably or at all for extended periods of time, plug insertion can remove a significant amount of the pain associated with the problem. Increased neck and back comfort also tend to be exhibited by patients.

The above benefits may also be experienced using devices or treatments such as contact lenses (with or without color or tint), eyeglasses (with or without tints, partial or total light blocks), prisms, tear dye, visors, blinders, filters, manipulation of head and neck position and muscle tension. These devices or treatments may be used alone or in combination with one or more of the above methods using the plugs for increasing the eye tear level to affect the above described linkages and can be used to alter these linkages thereby providing benefits for patients. As used herein, the terms light altering and light blocking may be used interchangeably. The terms at least partially altering encompass and include the term blocking.

Within the novel methods, in addition to altering eye moisture through total or partial blockage of the lacrimal system by use of punctal or lacrimal plugs or surgical or non-surgical closure, neuro-optometrists use a variety of other tools, such as, lenses, prisms and filters and other kinds of occluders to alter light signals. Each tool alters light in a different manner but they all change both the amount and direction of light entering the retina. Once the light strikes the tear layer, it travels through the cornea, lens, aqueous and vitreous to terminate at the retina. From the retina the light signals are converted into electrical signals which the brain processes. The retina is mapped onto the brain very precisely so when the light is angled in different ways, different parts of the brain are being stimulated. For instance, when the light is angled downward, more of the temporal lobes are being stimulated; when the light is angled upward, more of the parietal lobes are being stimulated. If blue filters are used on a patient, the light is bent more sharply than if red filters are used. The blue filters angle the light more toward the center of the eye; the longer wavelength of the red filters angle the light more toward the far retinal periphery.

Initially during neuro-optometric testing, patients display symptoms and the neuro-optometrist has to choose which method to use. The standard method of care is using lenses and the standard optometrist is taught in school that if the patient can't see, find what lens makes them see centrally and prescribe it for them. If lenses don't help enough and the patient is seeing double, the optometrist will typically use a non-yoked prism and if the patient still has problems, they will use a tint. Under one embodiment of the present invention, the preferred way instead begins with the yoked prism, which alters the center of gravity because the yoked prism will bend the light from above, below or from the side. As such, it will create a reflex reaction via non-visual retinal pathways of the patient's eyes pointing in the direction of the light. When a patient's eyes point in the direction of the light, his head will follow and then his body will shift, turn and twist to follow the light. This movement shifts his center of gravity and therefore a reflex reaction is created and affects how his eyes point.

Using the methods described herein, in certain applications for patients displaying certain symptoms of visual and non-visual retinal processing dysfunctions, prisms, lenses or filters would be used instead of punctal plugs. One example is a patient who is more nearsighted in one eye than the other. Another example is a patient who is sensitive to size changes in one eye but sensitive to depth changes in the other eye or if one eye is sensitive to astigmatism changes or axis changes and the other eye is not. The effectiveness of the intervention can be monitored by observing neck control during the Z-Bell Test and by measurements of aiming and focusing ranges while the patient is behind the phoropter.

In certain situations, if a patient wears a yoked prism, he may not require traditional eyeglass or contact lenses because the yoked prism makes the patient tip his head a different way and he sees comfortably and clearly. Some nearsightedness in children can be prevented by using this method. In one embodiment of this method of the present invention, a light filtering device would be used instead of a punctal plug if there's an additional symptom of central eyesight being imbalanced. The yoked prisms are available in different directions each affecting body awareness depending on the sensitivity of retinal processing systems and the angle at which light enters. The effectiveness of this intervention can be monitored by observing accuracy during the Z-Bell Test.

Another embodiment of a method is the use of an asymmetric amount of yoked prism, inducing an effect of a combination of yoked and non-yoked prisms at the same time. A non-yoked prism is a device that can affect the apparent location of a target but not the patient's center of gravity (whether it appears to be closer or farther) and it adjusts a patient's eyes in or out, as opposed to the yoked prisms which will adjust a patient's neck and head and affect the patient's center of gravity. The yoked prisms work subcortically and the non-yoked prisms work cortically. The non-yoked prisms include base-in and base-out prisms. The yoked prisms include base-up, base-down, base-left and base-right or combinations of any of them. Asymmetrical prisms can be used through which both yoked and non-yoked effects can be achieved at the same time. For example, a patient who needs 1½ base-in in the right eye and only 1 base-out in the left eye, can achieve a base-left effect with a small amount of base-in effect. This alteration of spatial orientation is important in some patients for remediation of visual and non-visual retinal processing dysfunctions. The effectiveness of this intervention can be monitored by observing accuracy during the Z-Bell Test.

Another device that can be used as a method is lenses that are designated in pluses and minuses, spheres and cylinders. In addition to the traditional usage of these lenses by all optometrists, they can be used to directly affect visual and non-visual retinal pathways altering spatial orientation and organization remediating imbalances in processing, integration and posture disorders The effectiveness of this intervention can be monitored by observing accuracy during the Z-Bell Test.

In patients with sensory system linkage dysfunctions, contact lenses as an embodiment of the present invention may be used for treatment. Each of the sensory inputs function at both subcortical and cortical levels. Contact lenses will bend the entering light into the eye in various ways striking the retinal sensors. Each of the retinal sensors is mapped onto the cortex and the mid-brain and the impact will affect balance, motion sickness, vertigo, concentration and attention levels, moods and anxiety as well as sensory integration and processing and therefore posture. Again, the Z-Bell Test can measure the alteration of spatial orientation and its effect.

Filters may be used as still another form of one embodiment of a method. There are many different types of filters, including tints, that may be used to alter spatial orientation and organization. Bluish tints bend light more toward the center of the retina and reddish tints bend light more toward the peripheral retinal sensors. Total (opaque) and partial (translucent) filters can be used to selectively block, partially or totally, retinal sensors in various locations, superior, inferior, left, right, central or peripheral. A neutral density filter is used as another method of the invention. Neutral density filters reduce light of all wavelengths or colors equally, lessening the overall amount of retinal stimulation. This provides a positive effect in many patients with processing, postural or sensory imbalances. The Z-Bell Test is useful to distinguish the precise amount and effects of filtering needed to balance the processing systems.

Visual processing is complex. FIG. 8 shows one embodiment of the Zelinsky Intervention-Response Chart, which separates and explains the various stages of visual development, and summarizes expected responses to different optometric interventions. Non-standard responses can provide information useful in identifying any deficient visual pathway(s), and the appropriate treatment or referral.

Other embodiments may use eyeglasses with or without tints and with or without partial or total light blocks for treatment as described herein. When a patient is exhibiting sensory integration difficulties, processing problems or developmental delays, eyeglasses can be used to alter the light entering the retina, and thus can have an effect on sleep disorders (via both the retinohypothalamic and the accessory optic pathways), attention deficit disorder (ADD) or various neurological impairments. The type of lenses would be measured with the patient both behind and outside the phoropter. During testing, the patient and the targets would be both stationary and moving. These tests can also be combined with the Padula Visual Midline Shift Test, the Z-Bell Test, a yoked prism walk and/or a fixation disparity test. Any of these tests would contribute to a determination of which type of eyeglasses would be best used for treatment. The results of these combinations of tests can have far-reaching effects in myriad fields of learning endeavors, including, but not limited to, languages, music, aviation and athletics.

The length of treatment required obviously varies with the extent of sensory system linkage dysfunctions and can be estimated only on a per patient basis, if at all. In most applications, the eyeglasses are a short-term requirement because they are typically used to provide a temporary spatial shift. But, after reorientation and linkage, a full series of treatments may still be necessary.

In yet another form, prisms are put into the glasses for the treatment method. As explained above, there are two different types of prisms, yoked and non-yoked. The yoked prisms angle light along the x and y axes and a patient will experience a reflex eye response and a head movement and shift of center of gravity. The yoked prisms then, in essence, trigger a compensatory movement in the hips to counterbalance the reflex so that the body reorients itself and remains balanced. The non-yoked prisms angle the light inward and outward long the Z-axis and cause the patient to adjust his shoulders in and out. When a patient is using the non-yoked prisms he gets more muscle tension in the shoulders because of shifting. When a patient is using the yoked prism he gets more muscle tension in the hips.

Patients who might benefit the most from the use as described above of yoked or non-yoked prisms, or both, are those who have processing difficulties, integration problems, imbalances, either congenital or acquired (such as with a traumatic brain injury) whether the imbalances, are neurological or biochemical, and patients with abnormal postures and scoliosis. The length of time a patient might need to wear the prisms would be about the same as described for the eyeglasses above. Also, a series of prisms would likely be used to continually alter spatial orientation. Treatment would depend on the extent and severity of the sensory linkage dysfunction. This dysfunction could be developmental or traumatic.

In yet other forms of treatment, tear dye can be used to achieve the benefits described herein for certain patients. Putting colored tear dye into the lacrimal system is similar to wearing a colored pair of eyeglasses. The main difference would be that the entire retinal input would be filtered to one wavelength. With colored eyeglasses, there is a combination from the side vision of white light and the center with filtered light. Testing can be done using a calorimeter that can determine which color is best for a patient exhibiting certain disorders. Different colors have different frequencies and bend the light different amounts. For example, the color blue bends light sharply, more toward the center of the eye. Red color bends light a little less sharply than blue. The colors with the longer wavelengths tend to go more towards the retinal periphery. The type of colored tear dye would be dependent upon which frequency was best for a particular patient. Again, the Z-Bell Test would monitor sensory linkages and help determine the proper color required. Because sometimes the color subjectively chosen on a conscious level does not match that chosen at an unconscious or subconscious level, the Z-Bell Test is more accurate than the patient.

In yet other embodiments, visors, blinders and filters can achieve similar positive treatment benefits by altering the balance between mangocellular and parvocellular pathways. These devices cut off or reduce the amount of entering light from different directions. When a visor is used, light could be angled one way or another. Blinders can be used for one side of a patient's face or extend from his nose and ear only. The most recent research shows that the peripheral retinal receptors are much more involved in how the central visual system is used. Blinders can also be in the form of a contact lens with a filtered or occluded section, partially or totally blocking some peripheral retinal signals.

In addition to altering spatial orientation, the retinal receptors are also connected via the retinotectal pathway and accessory optic pathway and the retinopretectal pathway. A neutral density filter is another method of altering these retinal connections embodied in the form of the present invention. One patient in particular, for example, had significant chemical exposure for a prolonged period of time. Her senses of smell and taste were both heightened to the extreme so that any exposure via her gustatory or olfactory systems was unbearable. For example, she was able to eat only twelve different foods in a rotation every three days, otherwise foods would burn her tongue, making it feel like she was always eating hot peppers. She went into anaphylactic shock from exposure to latex. Partially blocking her retinal pathways in only her right eye allowed her to maintain an expanded range of tolerance to airborne and ingested stimuli. The filters were used in this example to partially block the light on the non-visual retinal receptors to affect the smell and taste of the individual. In this example, a neutral density filter can be used as treatment. The Z-Bell Test with her eyes closed indicated where the neutral density filter would be the most useful. The test failed when the filter was placed over her left eye, but succeeded when the neutral density filter was positioned in front of her right eye. She was not aware of the placement of the filter (her eyes were closed) and yet she was consistent in her responses to the auditory portion of the Z-Bell Test. She was unable to locate the bell when no filters were placed in front of her eyes, or when the filter was in front of her left eye. She was only able to locate the sound when having the neutral density filter placed over her right eye. This pinpointed which eye and which receptors were playing havoc with her nervous system.

Yet other embodiments of the present invention may use weights to adjust head and neck position and neck muscle tension. When a weight is placed or positioned on a patient's shoulders, the increased tension reflexively pulls the eyes inward. The spinal accessory nerve is connected with the stemocleidomastoid muscle (SCM) in the neck and when either the trapezius muscle or the SCM is stimulated, there is a reflexive effect on eye movement. The whole sense of convergence of the eyes is linked with neck control and when light enters (when the eyes adjust inward or if the shoulders are hunched up or tense) the eyes will adjust inward. Then, when light strikes a different part of the retina, visual and non-visual input to the nervous system is altered, affecting posture and spatial orientation. The Z-Bell Test measures the effectiveness of the change in orientation and thereby indicates the optimal weight position and which muscles are not neurologically functioning properly.

For example, in one application for children who have ADD and autism, when weights were used to press down on their shoulder and neck muscles their auditory localization ability changed. This application can also be used for children who cannot easily isolate sounds from a noisy background or pay attention in school. Placing a weight on one shoulder allows the child to localize a teacher's voice and pay attention by integrating his sensory systems and thus enhancing his processing abilities.

When a device such as a weight is used to alter muscle tension, one type of device can be placed on the shoulder because it will affect the neck and the neck and the eyes are connected thereby creating a response. In other applications weights can be used on the ankle or the hips because anything that shifts the center of gravity so that a person shifts his weight in different ways that will ultimately affect the person's eyes. Eye function is intimately linked to a sense of balance. There are reflex connections to the eyes even from the ankles. As the ankles move, the eyes will make a compensatory movement. Any type of weights located anywhere on the body will have an effect on the eyes and thus an effect on the input to the visual and non-visual retinal sensors. For example, auditory localization is changed by the shoulder weights or by ankle position.

Specific embodiments of novel methods for diagnosis and/or treatment of processing difficulties, integration problems, imbalances and abnormal postures have been described for the purpose of illustrating the manner in which the forms of inventions are made and used. It should be understood that the implementation of other variations and modifications of the multiple inventions and their various aspects will be apparent to one skilled in the art, and that the inventions are not limited by the specific embodiments described. Therefore, it is contemplated to cover the present inventions, any and all modifications, variations, or equivalents that fall within the true spirit and scope of the basic underlying principles disclosed and claimed herein.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for diagnosis and treatment for a patient having processing difficulties, integration problems, imbalances or abnormal postures, comprising the steps of:

identifying a patient having retinal signal processing problems creating at least one negative medical condition; and blocking at least a portion of the patient's lacrimal drainage system to achieve improved retinal signal processing for the patient and improve at least one of the patient's negative conditions.

2. The method of claim 1 further comprising the step of at least partially altering at least some of the light entering at least one of the patient's eyes using a light altering device selected from the group consisting of opaque contact lenses, colored contact lenses, non-colored contact lenses, translucent or enhancer tinted contact lenses, visible tint contact lenses, eyeglass lenses with or without tints or filters or prisms, occluders, neutral density filters, partial or total light blocks, prisms, tear-dye, visors, blinders and non-lacrimal occluders.

3. The method of claim 1 further comprising the step of modifying the patient's posture.

4. The method of claim 1 further comprising the step of modifying the patient's head position.

5. The method of claim 1 further comprising the step of modifying the patient's muscle tension.

6. A method for diagnosis and treatment for a patient having processing difficulties, integration problems, imbalances or abnormal posture comprising the steps of:
   identifying a patient having retinal signal processing problems;
   providing a means for at least partially blocking at least a portion of the patient's punctum; and
   achieving improved retinal signal processing for the patient.

7. The method of claim 6 wherein the means for at least partially blocking comprises one or more punctal plugs.

8. The method of claim 7 further comprising the step of at least partially altering at least some of the light entering at least one of the patient's eyes using a light altering device selected from the group consisting of opaque contact lenses, colored contact lenses, non-colored contact lenses, translucent or enhancer tinted contact lenses, visible tint contact lenses, eyeglass lenses with or without tints or filters or prisms, occluders, neutral density filters, partial or total light blocks, prisms, tear-dye, visors, blinders and non-lacrimal occluders.

9. The method of claim 7 further comprising the step of modifying the patient's posture.

10. The method of claim 7 further comprising the step of modifying the patient's head position.

11. The method of claim 7 further comprising the step of modifying the patient's muscle tension.

12. A method for diagnosis and treatment for a patient having processing difficulties, integration problems, imbalances or abnormal postures, comprising the steps of:
   identifying a patient experiencing sensory system linkage dysfunction creating at least one undesirable condition;
   providing a means for at least partially altering at least a portion of the patient's puncta; and
   achieving improvement in at least one of the patient's conditions selected from the group consisting of mood disorders; anxiety; sleep disorders; stomach disorders; motion sickness; minimal flexibility in range of motion of muscles; lack of proper hip and neck stability; inability to properly perform basic tasks; attention disorder; lack of concentration; cognition; lack of creativity; articulation; expressive and receptive language; poor handwriting; poor reading fluency of both words and music; deficient reading comprehension; sensory integration; eye movement control; deficient note taking in classroom situations; deficient performance in sports; auditory localization ability; motor control and motor planning of both gross and fine muscles at both reflexive and cortical levels; lack of proper hearing of musical pitch, timbre, rhythm, volume and frequency; speed of entering sounds; lack of energy; eye strain; muscle tension; lack of stabilized balance; tinnitus; vertigo; lack of proper or poor spatial orientation; poor organization; and deficient sense of balance.

13. The method of claim 12 further comprising the step of at least partially altering at least some of the light entering at least one of the patient's eyes using a light altering device selected from the group consisting of opaque contact lenses, colored contact lenses, non-colored contact lenses, translucent or enhancer tinted contact lenses, visible tint contact lenses, eyeglass lenses with or without tints or filters or prisms, occluders, neutral density filters, partial or total light blocks, prisms, tear-dye, visors, blinders and non-lacrimal occluders.

14. The method of claim 12 further comprising the step of modifying the patient's posture.

15. The method of claim 12 further comprising the step of modifying the patient's head position.

16. The method of claim 12 further comprising the step of modifying the patient's muscle tension.

17. The method of claim 12 wherein the means for at least partially altering is at least one punctal plug.

18. The method of claim 12 wherein the means for at least partially altering is achieved by surgically closing at least part of the lacrimal system.

19. A method for a visual test for a patient comprising the steps of:
   instructing a patient to position the patient's hands at the patient's sides;
   selecting a location in front of the patient within a test zone between the patients shoulders and above the patient's armpits;
   using a means for a visual aid located in the selected location;
   instructing the patient to close the patient's eyes and visualize the means for a visual aid;
   requesting the patient to touch the target with at least one finger;
   scoring the test results;
   repeating the test as required for different selected locations;
   analyzing the test results; and
   diagnosing spatial perception with visual fibers.

20. The method of claim 19 whereby the means for a visual aid is the handle of a bell.

21. A method for an auditory and visual test for a patient, comprising the steps of:
   performing at least a portion of the Z-Bell Test on the patient,
   analyzing the test results; and
   determining the stability of sensory integration and retinal receptor sensitivity.

22. The method of claim 21 further comprising the step of evaluating the presence of residual primitive reflexes.

23. The method of claim 21 further comprising the step of diagnosing sensory linkages of non-visual fibers.

24. The method of claim 21 further comprising the step of diagnosing spatial perception with visual fibers.

25. The method of claim 21 further comprising the step of modifying the sound frequencies used during the Z-Bell Test and evaluating the flexibility of spatial orientation and the tolerance range of stray light.

26. The method of claim 25 further comprising the step of observing the manner in which the patient attempts to reach for sound locations and isolating the patient's neck, shoulder and eye movement to determine the presence of primitive reflexes.

27. The method of claim 21 further comprising the step of evaluating the patient's preferred auditory and visual frequencies.

* * * * *